United States Patent
Schaetzl et al.

(10) Patent No.: US 9,974,771 B2
(45) Date of Patent: May 22, 2018

(54) COMPOSITIONS AND METHODS FOR REDUCING PRION LEVELS

(71) Applicants: OHIO STATE INNOVATION FOUNDATION, Columbus, OH (US); UTI LIMITED PARTNERSHIP, Calgary (CA)

(72) Inventors: Hermann M. Schaetzl, Calgary (CA); Basant Abdulrahman, Calgary (CA); Sabine Gilch, Calgary (CA); Alexander Zukiwski, Clarksburg, MD (US); Stefan Proniuk, Austin, TX (US)

(73) Assignees: OHIO STATE INNOVATION FOUNDATION, Columbus, OH (US); UTI LIMITED PARTNERSHIP, Calgary (CA)

( * ) Notice: Subject to any disclaimer, the term of this patent is extended or adjusted under 35 U.S.C. 154(b) by 0 days. days.

(21) Appl. No.: 15/445,964

(22) Filed: Feb. 28, 2017

(65) Prior Publication Data

US 2017/0326108 A1 Nov. 16, 2017

Related U.S. Application Data

(60) Provisional application No. 62/302,006, filed on Mar. 1, 2016.

(51) Int. Cl.
*A61K 31/415* (2006.01)

(52) U.S. Cl.
CPC .................... *A61K 31/415* (2013.01)

(58) Field of Classification Search
CPC .................................... A61K 31/415
USPC ......................................... 514/406
See application file for complete search history.

(56) References Cited

U.S. PATENT DOCUMENTS

2011/0015242 A1    1/2011   Chen

OTHER PUBLICATIONS

Heiseke et al. Journal of Neurochemistry, (2009), vol. 109, pp. 25-34 (disclosed by Applicants in the IDS).*
Gao et al. Cancer Research, (2008), vol. 68, pp. 9348-9357 (disclosed by Applicants in the IDS).*
Prusiner, S.B. (1982). Science 216, 136-144.
Prusiner, S,B, (1998). Proc. Natl. Acad. Sci. USA 95, 13363-13383.
Nunziante, M., Gilch, S., Schatzl, H.M. (2003). Chembiochem. 4, 1268-1284.
Gilch, S., Krammer, C., Schatzl, H.M. (2008). Expert Opin. Biol. Ther. 8, 923-940.
Krammer, C., Vorberg, I, Schatzl, H.M., Gilch, S. (2009). Infect. Disord. Drug Targets 9, 3-14.
Ertmer, A. Gilch, S., Yun, S.W., Flechsig, E., Klebl, B., Stein-Gerlach, M., Klein, M.A., Schatzl, H.M. (2004). J. Biol. Chem. 279, 41918-41927.
Ertmer, A., Huber, V., Gilch, S., Yoshimori, T., Erfle, V., Duyster, J., Elsasser, H.P., Schatzl, H.M. (2007). Leukemia 21, 936-942.
Aguib, Y., Heiseke, A., Gilch, S., Riemer, C., Baier, M., Schatzl, H.M., Ertmer, A. (2009). Autophagy 5, 361-369.
Heiseke, A., Aguib, Y., Riemer, C., Baier, M., Schatzl, H.M. (2009). J. Neurochem. 109, 25-34.
Heiseke, A., Aguib, Y., Schatzl, H.M. (2010). Curr. Issues Mol. Biol. 12, 87-98.
Schatzl, H., Laszlo, L., Holtzman, D.M., Tatzelt, J. Weiner, R.I., Mobley, W., Prusiner, S.B. (1997). J. Virol. 71, 8821-8831.
Gilch, S., K. F. Winklhofer, M. H. Groschup, M. Nunziante, R. Lucassen, C. Spielhaupter, W. Muranyi, D. Riesner, J. Tatzelt, H.M. Schatzl. (2001). EMBO J. 20, 3957-3366.
Taguchi, Y., Mistica, A. M., Kitamoto, T., Schatzl, H. M. (2013) PLoS Pathog. 9, e1003466.
Maas, E., Geissen, M., Groschup, M.H., Rost, R., Onodera, T., Schatzl, H.M., Vorberg, I. (2007). J. Biol. Chem. 282, 18702-18710.
Qi, Y., Wang, J.K., McMillian, M., Chikaraishi, D.M. (1997). J. Neurosci. 17, 1217-1225.
Kuma, A., Hatano, M., Matsui, M., Yamamoto, A., Nakaya, H., Yoshimori, T., Ohsumi, Y., Tokuhisa, T., Mizushima, N. (2004) Nature 432, 1032-1036.
Orru, C.D., Wilham, J.M., Vascellari, S., Hughson, A.G., Caughey, B. (2012). Prion 6, 147-152.
John, T.R., Schatzl, H.M., Gilch, S.(2013). Prion 7, 253-258.
International Search Report and Written Opinion of PCT Application No. PCT/US2017/020053 dated May 26, 2017.
Gao, et al., "OSU-03012, a Novel Celecoxib Derivative, Induces Reactive Oxygen Species-Related Autophagy in Hepatocellular Carcinoma," Cancer Research, Nov. 15, 2008, vol. 68, pp. 9348-9357.

* cited by examiner

*Primary Examiner* — Yong Chu
(74) *Attorney, Agent, or Firm* — Potomac Law Group, PLLC; Jeremy A. Cubert, Esq.

(57) ABSTRACT

Compositions and methods for reducing the level of prions in a prion-infected cells or host by exposing prion infected cells, tissues and organs to AR-12 and the AR-12 analog AR-14 to reduce the prion level by at least about 90%.

12 Claims, 19 Drawing Sheets

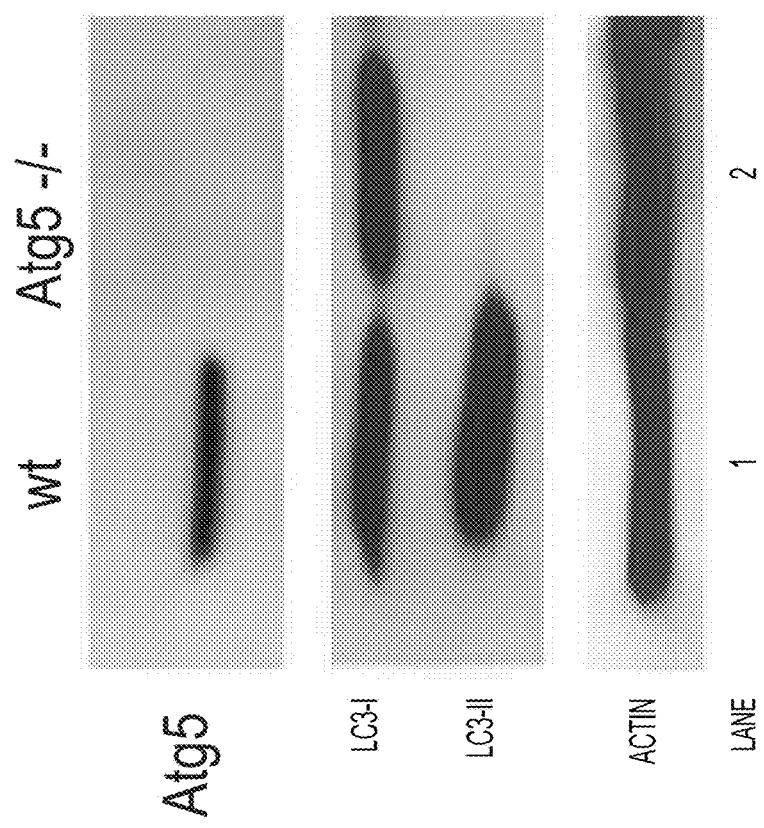

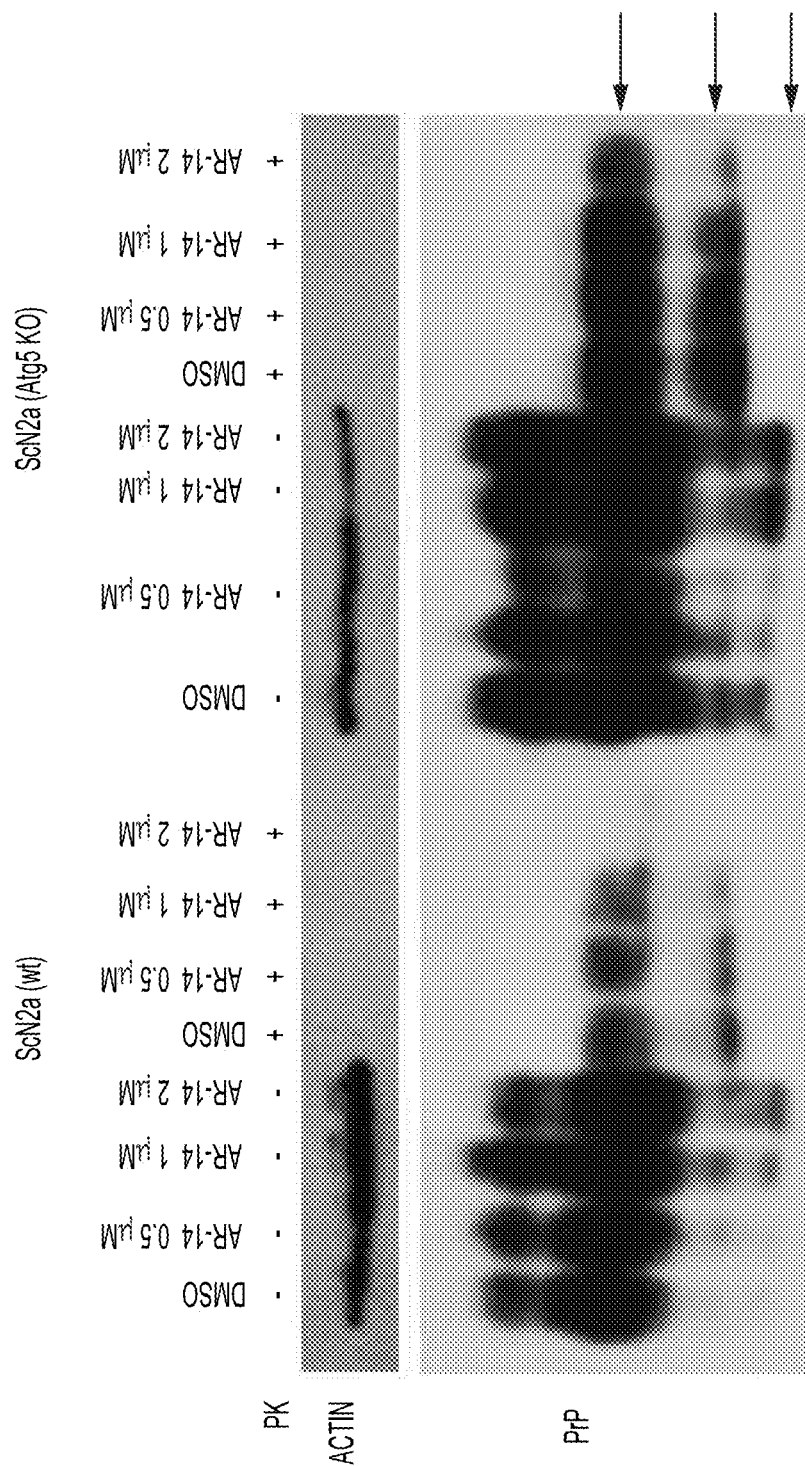

COMPOSITIONS AND METHODS FOR REDUCING PRION LEVELS

PRIORITY CLAIM

This application claims priority to U.S. Provisional Patent Application Ser. No. 62/302,006, filed Mar. 1, 2016. The above referenced application is incorporated herein by reference as if restated in full.

All references cited herein, including but not limited to patents and patent applications, are incorporated by reference in their entirety.

BACKGROUND

Prion diseases or transmissible spongiform encephalopathies (TSEs) are fatal infectious neurodegenerative disorders in man and animals (Prusiner 1982, 1998). Examples are Creutzfeldt-Jakob disease (CJD), variant CJD (vCJD), variably protease-sensitive prionopathy (VPSPr), Gerstmann-Sträussler-Scheinker syndrome (GSS), fatal familial insomnia (FFI), and kuru in humans; bovine spongiform encephalopathy (BSE) or mad cow disease in cattle, scrapie in sheep and goat, and chronic wasting disease (CWD) in cervids. Prions use template-directed refolding of the normal cellular prion protein ($PrP^c$) into the pathologic isoform $PrP^{Sc}$ for propagation (Prusiner 1982, 1998). This epigenetic process does not involve the coding of nucleic acids in the infectious agent and is solely based on change in protein conformation.

In humans, prion disease can be initiated by a spontaneous event, with genetic linkage passing from generation to generation within families, or acquired by infection. Examples of routes for infectious prion transmission include blood transfusions, dura mater grafts, and contaminated human growth hormone or contaminated medical instruments (iatrogenic prion diseases). Although rare, every year about 8,000 people die of sporadic and genetic prion diseases worldwide, and patients with genetic predisposition to prion infection can be diagnosed long before the onset of clinical disease presentation. As a result of BSE, there is evidence that between 1:10,000 and 1:20,000 in the general population of U.K. are infected with vCJD prions and are incubating the disease. So far, there is no established therapy or prophylaxis for human prion diseases. The major limitations of experimental anti-prion drugs include severe side effects observed in animal models and inability of the investigational drug to cross the blood brain barrier (BBB).

Cell culture models persistently infected with prions are typically used to screen potential anti-prion compounds for activity (Nunziante et al., 2003; Gilch et al., 2008; Krammer et al., 2009). In these models, treated and control cells are analyzed for the amount of $PrP^{Sc}$, which serves as a surrogate marker for prion infectivity. In this physiological system, the cellular and molecular requirements for conversion and cellular turnover of prions are considered, whereas most in vitro assays only test for interference in the physical interaction of $PrP^c$ and $PrP^{Sc}$ (Nunziante et al., 2003; Gilch et al., 2008; Krammer et al., 2009). These requirements include, for example, the proper subcellular localization and trafficking of $PrP^c$ and $PrP^{Sc}$ as well as the degradation kinetics of $PrP^{Sc}$. Validation of potential drug targets can be performed in prion-infected animal models.

A promising experimental anti-prion strategy is the induction of autophagy. Autophagy is a basic cellular program for degradation and recycling of cytosolic proteins, protein aggregates, and organelles. Published data shows that autophagy is a potent modifier of the cellular clearance of prions and that drug induced autophagy shifts the delicate equilibrium between propagation and clearance of prions towards the latter (Ertmer et al., 2004, 2007; Aguib et al., 2009; Heiseke et al., 2009, 2010). There is proof-of-concept evidence that drug-induced activation of autophagy can delay or diminish prion diseases in animal models (Aguib et al., 2009; Heiseke et al., 2009).

AR-12 (a.k.a. OSU-03012) has been previously shown to exhibit anti-tumor, antiviral, anti-fungal and anti-bacterial activity. It is thought that AR-12 induces autophagy of cells harboring intracellular microbes. However, the anti-prion activity of AR-12 has not been previously shown.

SUMMARY

Aspects described herein provide methods and compositions for reducing the level of prions in prion-infected cells, tissues or organs, by exposing prion-infected cells, tissues or organs to AR-12 by administering AR-12 to a host with a prion infection in an amount sufficient to reduce the level of prions in the prion-infected cells, tissues or organs by at least about 90% compared to prion-infected cells, tissues, organs that have not been exposed to AR-12 in short-term treatments (e.g., 3 days) and to substantially cure infected cells from prion infection in long-term treatments (e.g., 20 days). In this aspect, the term "substantially cure" means reducing the amount of prions in infected cells by about 100% or below the detectable level.

In another aspect, prion infected cells, tissues or organs are exposed to AR-12 in an amount sufficient to achieve a concentration of at least about 1 µM in the prion-infected cells, tissues or organs. In another aspect, the concentration can be between about 1 µM and 3 µM.

The AR-12 analog AR-14 is also effective in reducing the level of prions in prion-infected cells. In one aspect, AR-14 can reduce the prion level in prion-infected cells, tissues, or organs by at least about 90% at nanomolar levels (e.g., less than about 1 µM) in short-term treatments (e.g., 3 days) and to substantially cure infected cells from prion infection in long-term treatments with a 2 µM treatment concentration (e.g., 20 days).

BRIEF DESCRIPTION OF THE DRAWINGS

The feature and nature of the present disclosure will become more apparent from the detailed description set forth below when taken in conjunction with the accompanying drawings.

FIG. 8A shows the establishment of a knock-out of Atg5 (autophagy gene) clone of N2A persistently prion-infected cells;

FIG. 8C is an exemplary immunoblot showing the PrP banding pattern for wild-type ScN2A cells (left panel) and autophagy-deficient Atg5-KO ScN2a cells (right panel) after treatment with control (DSMO) or AR-14 at three concentrations, with or without PK and actin used as a loading control.

DETAILED DESCRIPTION

Figure 1:
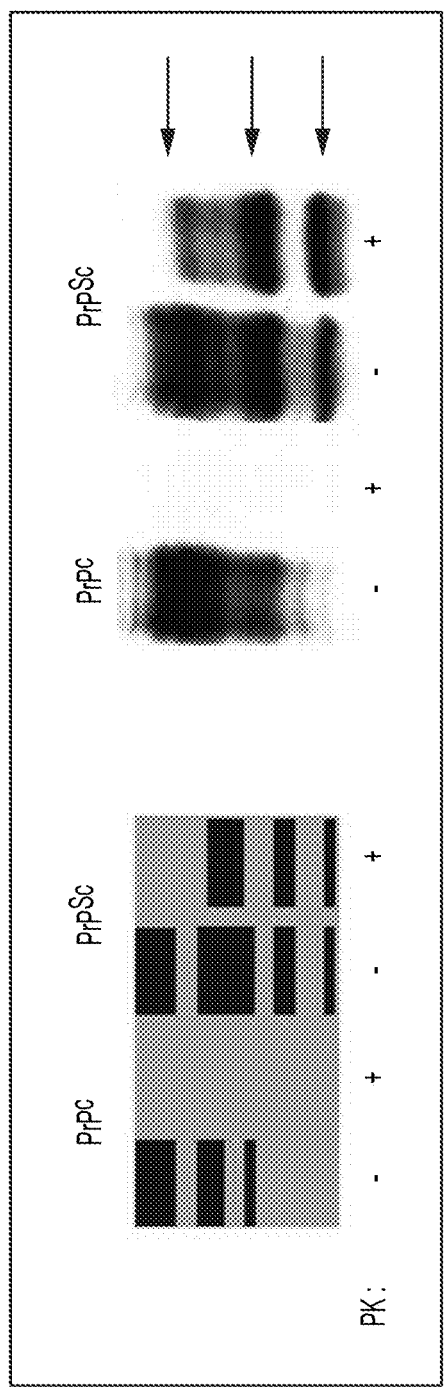
FIG. 1 is an immunoblot showing the relative proteinase K (PK) resistance of $PrP^{Sc}$ compared to $PrP^c$ (e.g., left panel/scheme shows a typical 3-band pattern, right panel/immunoblot shows comparative pattern of $PrP^c$ and $PrP^{Sc}$)

The disclosed methods and compositions below may be described both generally as well as specifically. It should be noted that when the description is specific to an aspect, that aspect should in no way limit the scope of the methods. All references cited herein are hereby incorporated by reference in their entirety.

The term "prion," as used herein, refers to unconventional infectious particles which are the causal agents of prion diseases in humans and animals and fatal infectious neurodegenerative disorders. Prions are composed of the pathological isoform $PrP^{Sc}$ of the prion protein, which serves as a surrogate marker for prion infectivity.

Aspects described herein provide methods of reducing the level of prions in prion-infected cells, tissues or organs, by exposing prion-infected cells, tissues or organs to AR-12 in an amount sufficient to reduce the level of prions in the prion-infected cells, tissues or organs by at least about 90% compared to prion-infected cells, tissues, organs that have not been exposed to AR-12. In another aspect, the prion level is reduced by at least about 50% (short-term treatment, e.g., 3 days) or prion-infected cells are substantially cured from prion infection (long-term treatment, e.g., 20 days).

In yet another aspect, prion infected cells, tissues or organs are exposed to AR-12 in an amount sufficient to achieve a concentration of at least about 1 µM in the prion-infected cells, tissues or organs. In another aspect, prion infected cells, tissues or organs are exposed to AR-12 in an amount sufficient to achieve a concentration of between about 1 µM and 3 µM in the prion infected cells, tissues, or organs. In a further aspect, the amount of AR-12 the prion infected cells, tissues, and organs are exposed to is sufficient to reduce the prion level by about 50% to about 90%, or substantially cures the prion-infected cells in long-term treatments. In these aspects, exposure to AR-12 does not result in substantial cytotoxicity of the prion infected cells.

As used herein, the term "cytotoxicity" refers to the quality or effect of a chemical, drug or compound being toxic to cells. The toxic effects on individual cells. The toxic effect on individual cells can then result in cell death, tissue necrosis and organ dysfunction or failure.

Aspects described herein provide methods of reducing the level of prions in prion-infected cells, tissues or organs, by exposing prion-infected cells, tissues or organs to AR-14 in an amount sufficient to reduce the level of prions in the prion-infected cells, tissues or organs by at least about 90% compared to prion-infected cells, tissues, organs that have not been exposed to AR-14. In another aspect, the prion level is reduced by at least about 50% (short-term treatment, e.g., 3 days) or prion-infected cells are substantially cured from prion infection (long-term treatment, e.g., 20 days).

In yet another aspect, prion infected cells, tissues or organs are exposed to AR-14 in an amount sufficient to achieve a concentration of at least about 0.5 µM in the prion-infected cells, tissues or organs. In another aspect, prion infected cells, tissues or organs are exposed to AR-14 in an amount sufficient to achieve a concentration of between about 0.5 µM and 2 µM in the prion infected cells, tissues, or organs. In a further aspect, the amount of AR-14 the prion infected cells, tissues, and organs are exposed to is sufficient to reduce the prion level by about 50% to about 90%, or substantially cures the prion-infected cells in long-term treatments. In these aspects, exposure to AR-14 does not result in substantial cytotoxicity of the prion infected cells.

As used herein, the term AR-12 refers to ($C_{26}H_{19}F_3N_4O$ and 2-amino-N-(4-(5-(phenanthren-2-yl)-3-(trifluoromethyl)-1H-pyrazol-1-yl)phenyl)acetamide)), having the following structure:

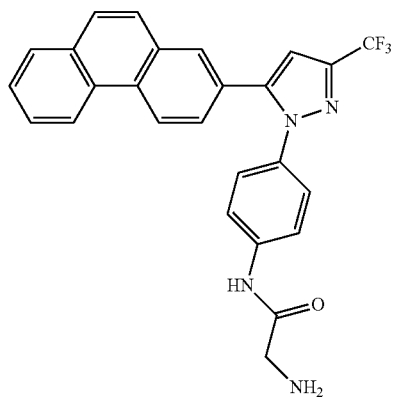 [SMILES: NCC(=O)Nc1ccc(-n2nc(C(F)(F)F)cc2-c2ccc3c(ccc4ccccc43)c2)cc1]

The term "AR-12" also includes, for example, analogs of AR-12 (e.g., the compounds described in U.S. Pat. Nos. 7,576,116, 8,546,441, 8,541,460, 8,039,502, and 8,080,574 hereby incorporated by reference in their entirety).

As used herein, AR-14 refers to a compound having the following structure:

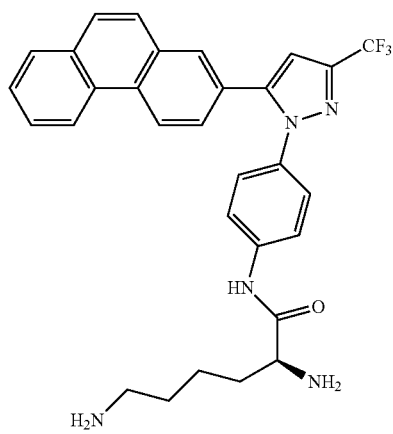 [SMILES: NCCCC[C@H](N)C(=O)Nc1ccc(-n2nc(C(F)(F)F)cc2-c2ccc3c(ccc4ccccc43)c2)cc1]

The relative resistance of PrP$^{Sc}$ to proteinase K (PK) digestion can be used as a diagnostic tool to distinguish between PrP$^c$ and PrP$^{Sc}$. In this aspect, lysates of cells or tissues are digested with proteinase K (PK) under defined standard conditions and analyzed in an immunoblot. As shown in FIG. 1, PrP$^c$ is completely sensitive to PK digestion. PrP$^{Sc}$ is only partially sensitive to PK digestion and becomes degraded solely at the N$^-$ terminus. The left panel of FIG. 1 shows situation schematically, right panel depicts a typical immunoblot result. For persistently prion-infected cells, a typical 3-banding pattern is obtained following PK digestion (+PK), representing N-terminally truncated un-glycosylated, single- and double-glycosylated PrPSc (see arrows).

Proteinase K (PK) was obtained from Roth (Karlsruhe, Germany), Pefabloc inhibitor was from Roche (Mannheim, Germany). Cell culture media and solutions were obtained from Invitrogen (Karlsruhe, Germany). N-Lauryl-sarcosine was purchased from Sigma-Aldrich (Munich, Germany). Immunoblotting was done using the enhanced chemiluminiscence blotting technique (ECL plus) from Amersham Corporation (Buckinghamshire, UK). The test AR compounds were dissolved in DMSO at a stock solution of 1 mM and stored at −20° C. The monoclonal anti-PrP antibody (mAb) 4H11 was generated using a dimeric murine PrP as an immunogen (Ertmer et al., 2004). Mouse anti-β-actin mAb was from Sigma, mouse anti-LC3 mAb was obtained from nanoTools (nanoTools Antikörpertechnik GmbH & Co. KG, Teningen, Germany). Peroxidase-conjugated immunoglobulins for immunoblot analysis were obtained from Dianova (Hamburg, Germany).

Cell Culture

The mouse neuroblastoma cell line N2a [American Type Culture Collection (ATCC) CCL-131] and the persistently-prion infected ScN2a cell lines (22L-ScN2a, RML-ScN2a) have been described (Schatzl et al., 1997; Gilch et al., 2001; Taguchi et al., 2013). N2a cells deficient for Atg5 were prepared by CRISPR-Cas9 technology and characterized in immunoblot and DNA sequencing for successful Atg5 knock-out. Characterized single cell clones were then infected with 22L prions as described previously (Maas et al. 2007). Wild type mouse embryonic fibroblasts (MEF) have been described before (Kuma et al., 2004) and have been persistently infected with mouse-adapted prion strains 22L, RML and Me7. CAD5 (a central nervous system cat-echolaminergic cell line; Qi et al, 1997) and persistently prion-infected 22L-ScCAD cells were prepared as above. MEF cells were maintained in Dulbecco's modified Eagle's medium (DMEM), N2a cells in Opti-MEM Glutamax medium, both media containing 10% fetal calf serum (FCS), penicillin/streptomycin and glutamine in a 5% $CO_2$ atmosphere. CAD5 cells were cultured in OptiMEM Glutamax medium containing 10% bovine growth serum (BGS) and penicillin/streptomycin in a 5% $CO_2$ atmosphere.

Cell Lysis, Proteinase K (PK) Analysis and Immunoblot

Immunoblot analyses were performed as previously described (Schatzl et al., 1997; Gilch et al., 2001; Taguchi et al., 2013). Confluent cells were lysed in cold lysis buffer (10 mM Tris-HCl, pH 7.5; 100 mM NaCl; 10 mM EDTA; 0.5% Triton X-100; 0.5% sodium deoxycholate (DOC)) for 10 min. For proteinase K (PK) treatment, post-nuclear lysates were divided into two halves. One half was incubated with PK (20 µg/ml) for 30 min at 37° C. and digestion was stopped by addition of proteinase inhibitors (0.5 mM Pefabloc) and directly precipitated with methanol. The sample without PK treatment was directly supplemented with proteinase inhibitors and precipitated with methanol. After centrifugation for 25 min at 3,500 rpm (4° C.), the pellets were re-dissolved in THE buffer (50 mM Tris-HCl pH 7.5, 150 mM NaCl, 5 mM EDTA) and gel loading buffer (7% SDS, 30% glycerine, 20% Et-SH, 0.01% Bromphenol blue in 90 mM Tris-HCl pH 6.8) was added. After boiling for 5 min an aliquot was analyzed on 12.5% SDS-PAGE. Proteins were electrotransferred to polyvinylidene difluoride (PVDF) membrane (Amersham). Membranes were blocked with non-fat dry milk (5%) in Tris-buffered saline (TBST) (0.05% Tween 20, 100 mM NaCl, 10 mM Tris-HCl; pH 7.8), incubated overnight with the appropriate antibody at 4° C. and stained using enhanced chemiluminiscence blotting (ECL plus) kit from Amersham. To achieve equal loading of total protein for different samples in immunoblot analysis (e.g. comparison of $PrP^{Sc}$ amounts in different samples, or LC3-II levels), the same number of cells were plated and grown under identical conditions over specific periods. Cells were subsequently lysed in the same amount of lysis buffer. Precipitated proteins of each sample were resuspended in the same amount of THE buffer and supplemented with identical amounts of gel loading buffer. Equal volumes of each sample were then analyzed by 12.5% SDS-PAGE. In addition, immunoblots were stripped with anti-β-actin antibody to verify equal amounts of total protein loaded on gel for each sample. To allow comparison of endogenous LC3-II levels, intensity of LC3-II signals were measured relative to actin signals by densitometry analysis.

Viability Assay (XTT)

The viability of a cell population upon treatment with different compounds was determined with the XTT assay (Roche, Mannheim, Germany). Viability testing was mainly performed in uninfected cells. Data from our and other groups showed that viability in uninfected and persistently prion-infected N2a, CAD5 or MEF cells is substantially the same. Cells were plated at a density of $1.5 \times 10^4$ cells per well in 96 well plates. The following day, cells were treated for 72 h with various concentrations of the indicated compounds. Subsequently, 50 µl of the XTT reagent was added to each well. After incubation for 4 h, the absorption at 450 nm was measured with a FLUOstar Omega plate reader (BMG LABTECH, Offenburg, Germany). The average absorption of four control wells was set as 100% viability. The viability of treated cells was compared to the viability of DMSO (negative control) or Triton X-100 (positive control) treated cells.

Real-Time Quacking-Induced Conversion Assay (RT-QuIC)

A. Preparation of Recombinant Protein.

Preparation of recombinant prion proteins was performed as described (Orru et al., 2012). Briefly, mouse PrP (aa 23-231) was cloned into pET-41 plasmids, transformed into E. coli Rosetta, and bacteria cultured in LB media supplemented with kanamycin (0.05 mg/ml) and chloramphenicol (0.034 mg/ml). The Overnight Express Autoinduction System (Novagen, USA) was used to induce protein expression. Inclusion bodies were isolated from pelleted cells using Bug Buster Master Mix (Novagen, USA) and stored at −20° C. For purification of recombinant PrP, inclusion bodies were solubilized in (8 M guanidine-HCl, 100 mM Na-phosphate, 10 mM Tris-HCl, pH 8.0) and incubated on the rocker for 1 h at RT. Ni-NTA Superflow resin beads (Quiagen, USA) were incubated in denaturing buffer (6 M guanidine-HCl, 100 mM Na-phosphate, pH 8.0) for 1 h at RT. Solubilized inclusion bodies were centrifuged at 16,000×g for 5 min, the supernatant added to the beads and incubated for 1 h with gentle rocking. Beads were then packed into a XK16 glass column (GE Healthcare Life Sciences; USA; length 200 mm). Using an Amersham AKTA Explorer FPLC unit running with Unicorn software (5 version, GE Healthcare Life Sciences, USA), protein was refolded by a gradient from 100% denaturing buffer to 100% refolding buffer (100 mM Na-phosphate, 10 mM Tris-HCl, pH 8.0) over 4 h. The column was washed for 30 min with refolding buffer and proteins eluted using a linear gradient from 100% refolding buffer to 100% elution buffer (500 mM imidazole, 100 mM Na-phosphate, 10 mM Tris-HCl, pH 5.8). The central portions of the A280 UV peak were collected into dialysis buffer (10 mM Na-phosphate, pH 5.8). Purified protein was filtered using a 0.22 µm filter, transferred into a Slide-A-Lyzer dialysis cassette (MW 10 kDa; Thermo-Scientific, UA) placed into a 4 l beaker with dialysis buffer overnight at 4° C. with continuous stirring. Following dialysis, the protein solution was filtered again with a prewashed 0.22 µm Argos syringe filter. Protein concentration was measured using BCA protein assay (Thermo-Scientific, 23227), the solution aliquoted and kept in −80° C. until use.

B. RT-QuIC assay. Real-time QuIC was performed as described (John et al., 2013). Briefly, reactions were set up in assay buffer containing 20 mM Na-phosphate, pH7.4, 300 mM NaCl, 1 mM EDTA, 10 µM Thioflavin T and 0.1 mg/ml rPrP substrate. Ninety-eight µl aliquots were added to the wells of a black-walled 96-well optical bottom plate (Nalge Nunc International, Nunc, USA). Tenfold serial dilutions of brain homogenate or cell homogenate were prepared in 0.5 ml microtubes. Quadruplicate reactions were seeded with 2 µl of test solution for a final reaction volume of 100 µl. Reactions contained a final concentration of 0.002% SDS. Plates were sealed with Nunc Amplification Tape (Nalge Nunc International) and incubated in a FLUOstar Omega (BMG Labtech, Cary, N.C., USA) plate reader for 30 h. Reactions were incubated at 42° C., with cycles of 60 s shaking (700 revolutions per minute) and 60 s of rest throughout the incubation. ThT fluorescence measurements (450 nm excitation and 480 nm emission) were taken every 15 min. RT-QuIC data were averaged from four replicate wells and average values plotted against reaction time. Samples were scored positive if at least 50% of replicates reached a ThT fluorescence cut-off, which was calculated based on the average ThT fluorescence plus 5× standard deviation.

Figure 2A:
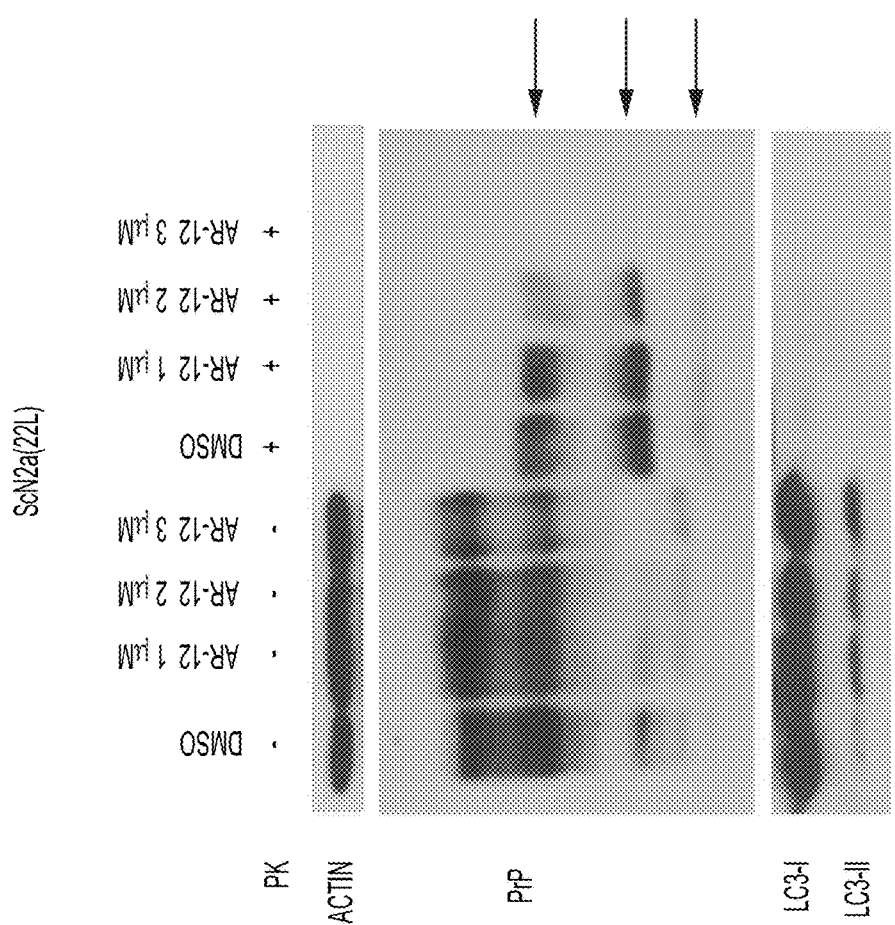
FIG. 2A is an exemplary immunoblot showing the PrP banding pattern following treatment of persistently prion infection neuronal cells (ScN2a) treated for 72 hours with three concentrations of AR-12, with (right panel) and without proteinase K digestion (PK) (left panel); actin (upper panel) was used as a loading control.

As shown in FIG. 2A, persistently prion (prion strain 22L) infected mouse neuronal cells (ScN2a cell line) were treated for 72 hours with the indicated concentrations of AR-12, and the cells were subjected to immunoblot analysis. Solvent only-treated cells (DMSO) were used as control. Cell lysates were split into two halves and one treated with proteinase K (PK; 20 µl/ml, 30 min at 37° C.) and subjected to SDS-PAGE and immunoblot analysis.

The immunoblot was developed with anti-PrP monoclonal antibody (mAb) 4H11 and the blot was re-probed with mAbs for actin (gel loading) and LC3 (autophagy marker). PrP$^{Sc}$ (right side, +PK; 3 glycoforms indicated by arrows) was dose-dependently reduced, to undetectable levels when treated for 3 days with a concentration of 3 µM (=100% reduction). Since PrP$^{Sc}$ has a very long half-life time in cultured cells (>24 h; see Ertmer et al., 2004), such a strong anti-prion effect after 3 days of treatment strongly indicates that AR-12 induces PrP$^{Sc}$ clearance as opposed to inhibiting PrP$^{Sc}$ propagation. LC3-II was induced about 2-fold, indicating induction of autophagy.

Figure 2B:
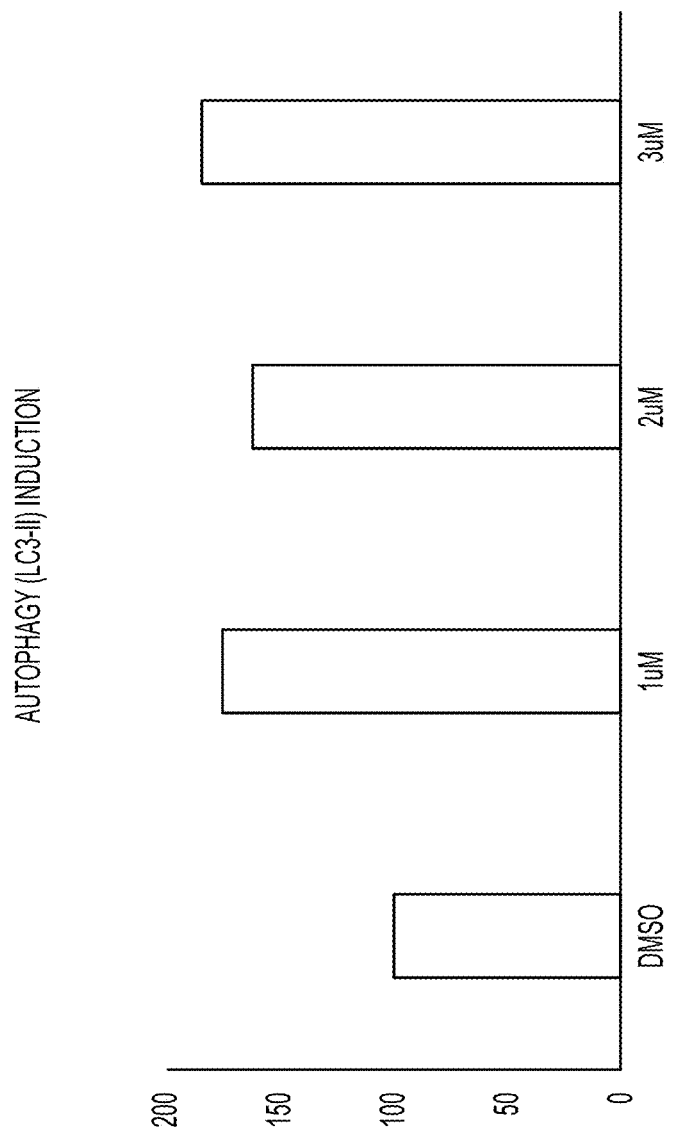
FIG. 2B illustrates an exemplary Autophagy Assay measuring LC3-II induction for control (DSMO) and three concentrations of AR-12.
Figure 2C:
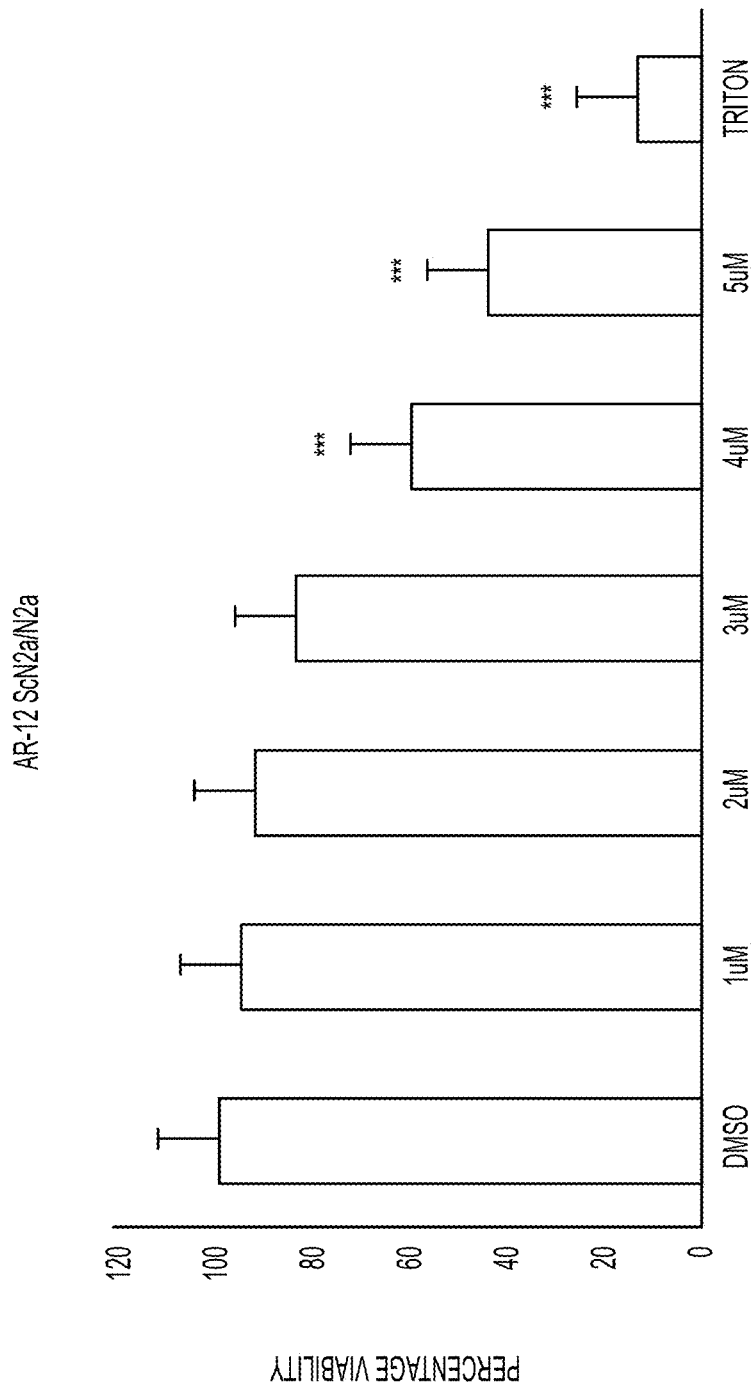
FIG. 2C illustrates an exemplary XTT Cytotoxicity Assay for control (DSMO) and five concentrations of AR-12; Triton X-100 treatment was used as a positive control (induction of cell death); asterisks indicate concentrations with statistically significant toxicity.

FIG. 2B shows an exemplary quantification of the autophagy induction at the indicated concentration of AR-12. FIG. 2C shows that exposing AR-12 to the cells was done at non-toxic concentrations (XTT toxicity assay).

Figure 3A:
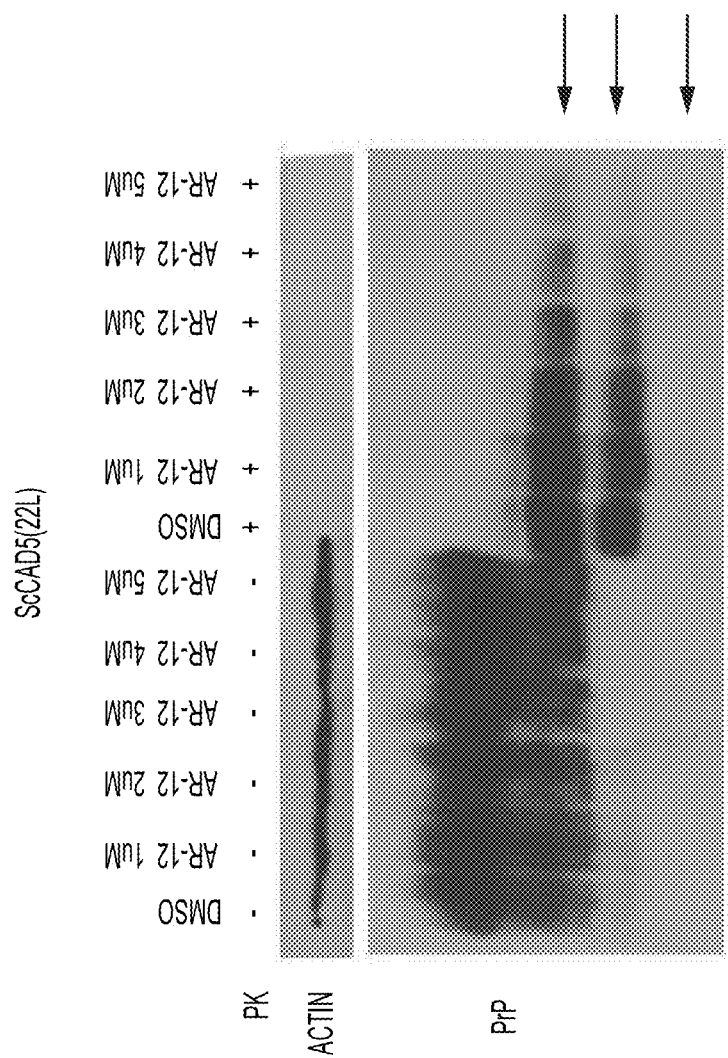
FIG. 3A is an exemplary immunoblot showing the PrP banding pattern for persistently prion infected ScCAD5 neuronal cells treated with DSMO (control) or 1, 2, 3, 4 or 5 µM AR-12 for 72 hours, with (right side) and without PK (left side); actin (upper panel) was used as a loading control.

FIG. 3A shows an exemplary effect of AR-12 administration on persistently prion-infected CAD5 cells (mouse neuronal cell line) over time. The CAD5 neuronal cells persistently infected with prions (mouse-adapted scrapie strain 22L; termed ScCAD5) were treated for 72 hours with 1-5 µM AR-12, and cells subjected to immunoblot analysis. Solvent only-treated cells (DMSO) were used as control. Cell lysates were split into two halves, and one treated with proteinase K (PK; 20 µl/ml, 30 min at 37° C.) and subjected to SDS-PAGE and immunoblot analysis. The immunoblot was developed with anti-PrP mAb 4H11, and the blot was re-probed with mAb for actin (gel loading; upper panel). PrP$^{Sc}$ levels (+PK; 3 glycoforms indicated by arrows) were reduced, although slightly less than in ScN2a cells. This result was expected, as ScCAD5 cells harbor more PrP$^{Sc}$ and therefore would need a longer treatment period. This data show that AR-12 is effective in another neuronal mouse cell type (derived from the central nervous system), confirming results described above for ScN2a cells.

Figure 3B:
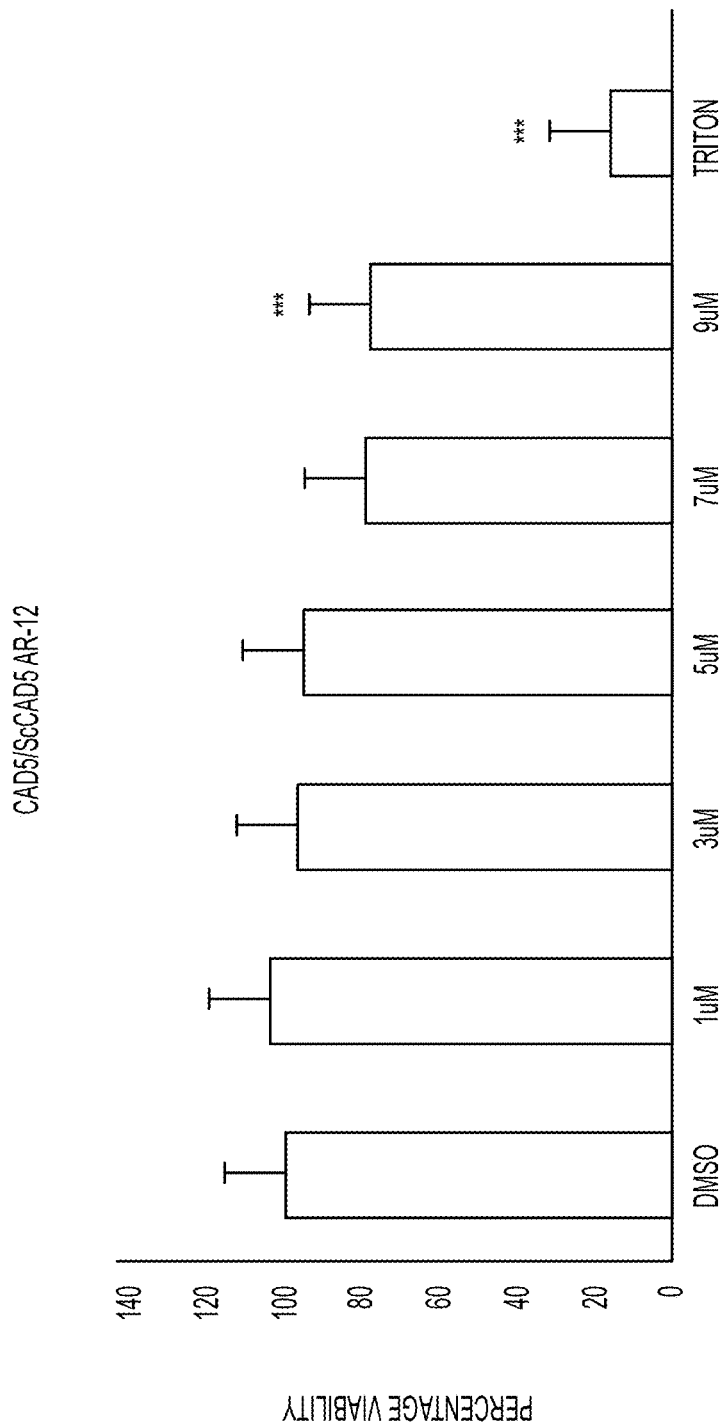
FIG. 3B illustrates an exemplary XTT Cytotoxicity Assay for control (DSMO) and five concentrations of AR-12; Triton X-100 treatment was used as a positive control (induction of cell death); asterisks indicate concentrations with statistically significant toxicity.

FIG. 3B shows that exposing AR-12 to the ScCAD5 cells was done at non-toxic concentrations (XTT toxicity assay).

Figure 4A:
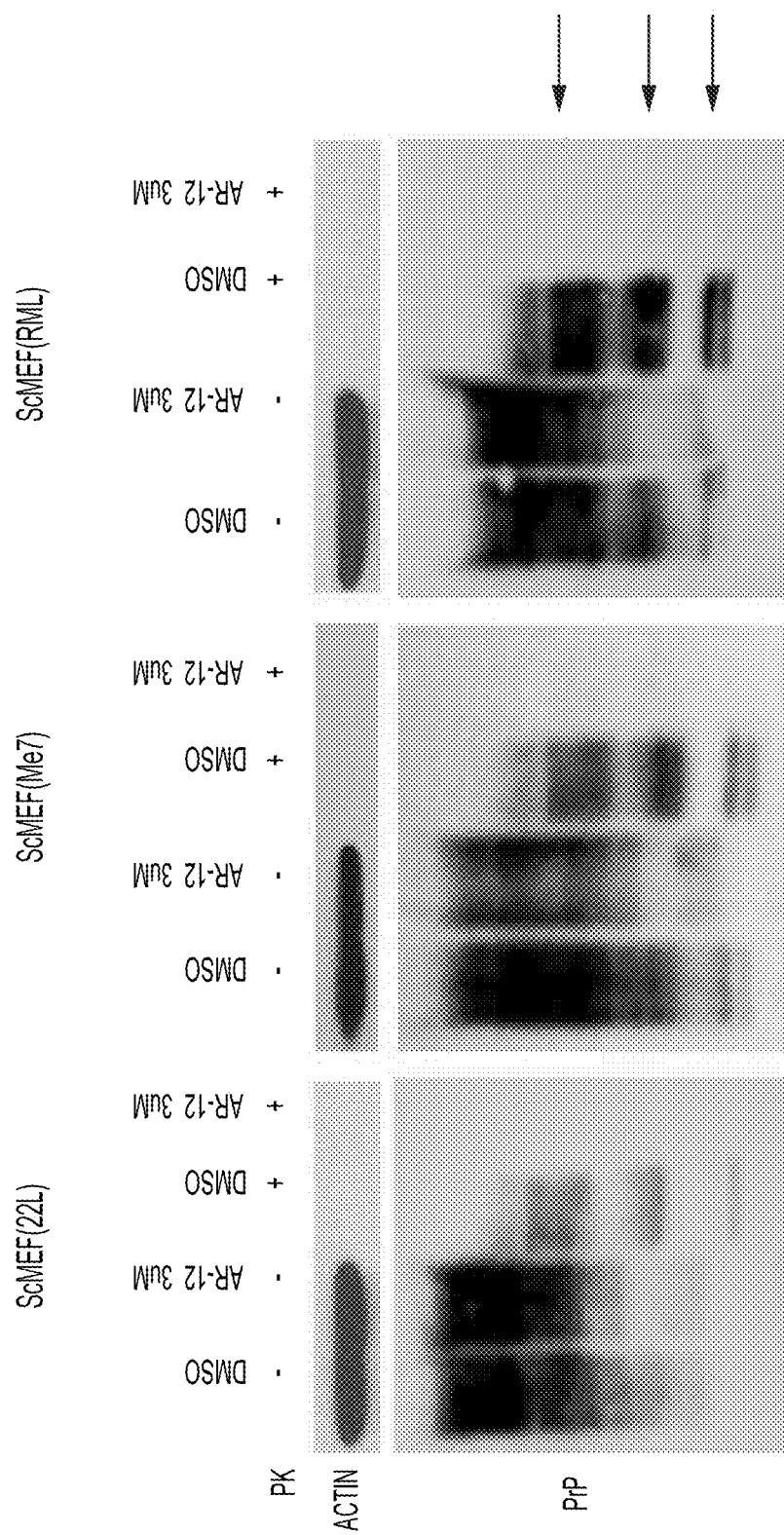
FIG. 4A is an exemplary immunoblot showing the PrP banding pattern for persistently prion infected ScMEF fibroblast cells (infected with prion strains 22L, Me7 and RML) treated with DSMO (control) or 3 µM AR-12 for 72 hours, with and without PK and actin (upper panel) used as a loading control.
Figure 5A:
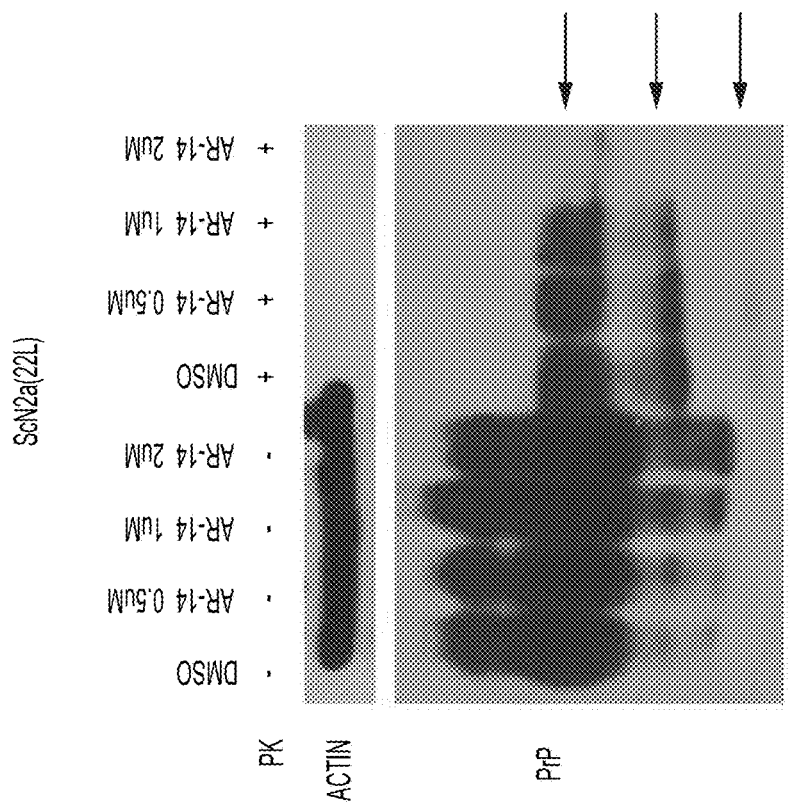
FIG. 5A is an exemplary immunoblot showing the PrP banding pattern following treatment of persistently prion infection neuronal cells (ScN2a) treated for 72 hours with three concentrations of AR-14 (0.5, 1 and 2 with (right panel) and without proteinase K digestion (PK) (left panel); actin (upper panel) was used as a loading control.

FIG. 4A shows an exemplary effect of AR-12 administration to persistently prion-infected mouse embryonic fibroblasts (ScMEFs, infected with mouse-adapted scrapie prion strains 22L, Me7 or RML). These fibroblast cells were treated for 72 hours with 3 µM AR-12, and the cells were subjected to immunoblot analysis. Solvent only-treated cells (DMSO) were used as control. Cell lysates were split into two halves and one treated with proteinase K (PK; 20 µl/ml, 30 min at 37° C.) and subjected to SDS-PAGE and immunoblot analysis. The immunoblot was developed with anti-PrP mAb 4H11 and the blot was re-probed with mAb for actin (gel loading; upper panel). PrP$^{Sc}$ (+PK; indicated by 3 arrows) was strongly reduced. As shown in FIG. 5A, AR-12 is also effective in a non-neuronal cell type, indicating a broad range of anti-prion activity that is not cell type-dependent. AR-12 was effective against three different prion strains (22L, RML and Me7), indicating a broad range of anti-prion activity against different prion strains.

Figure 4B:
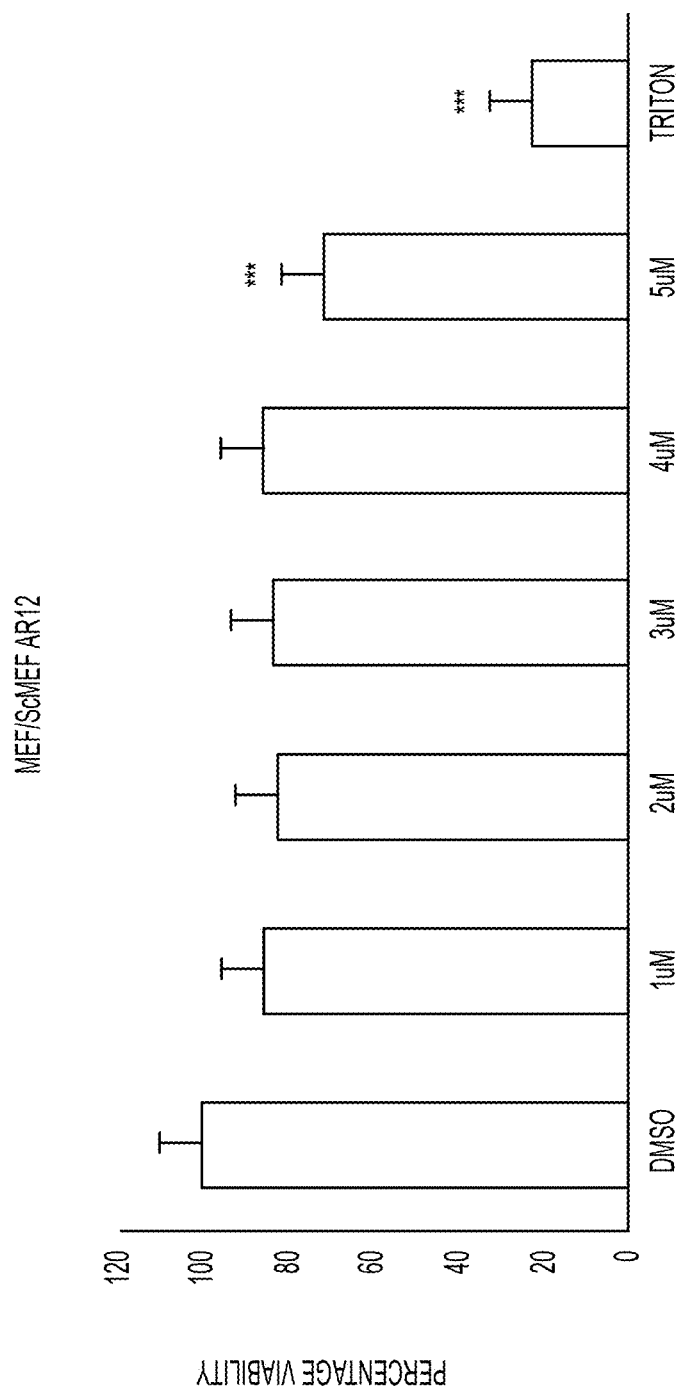
FIG. 4B illustrates an exemplary XTT Cytotoxicity Assay for control (DSMO) and five concentrations of AR-12; Triton X-100 treatment was used as a positive control (induction of cell death); asterisks indicate concentrations with statistically significant toxicity.

FIG. 4B shows that exposing AR-12 to the ScMEF cells was done at non-toxic concentrations (XTT toxicity assay).

FIG. 5A shows persistently prion (prion strain 22L) infected mouse neuronal cells (ScN2a cell line) treated for 72 hours with the indicated concentrations of AR-14 (0.5, 1 and 2 µM). Solvent only-treated cells (DMSO) were used as control. The cells were subjected to immunoblot analysis. Cell lysates were split into two halves and one treated proteinase K (PK; 20 µl/ml, 30 min at 37° C.) and subjected to SDS-PAGE and immunoblot analysis. The immunoblot was developed with anti-PrP mAb 4H11 and the blot was re-probed with mAb for actin (gel loading). PrP$^{Sc}$ (+PK; 3 glycoforms indicated by arrows) was dose-dependently reduced, to undetectable levels when treated for 3 days with a concentration of 2 (=100% reduction). Since PrP$^{Sc}$ has a very long half-life time in cultured cells (>24 h; see Ertmer et al., 2004), such a substantial anti-prion effect after 3 days of treatment strongly indicates that AR-14 induces PrP$^{Sc}$ clearance as opposed to inhibiting PrP$^{Sc}$ propagation.

Figure 5B:
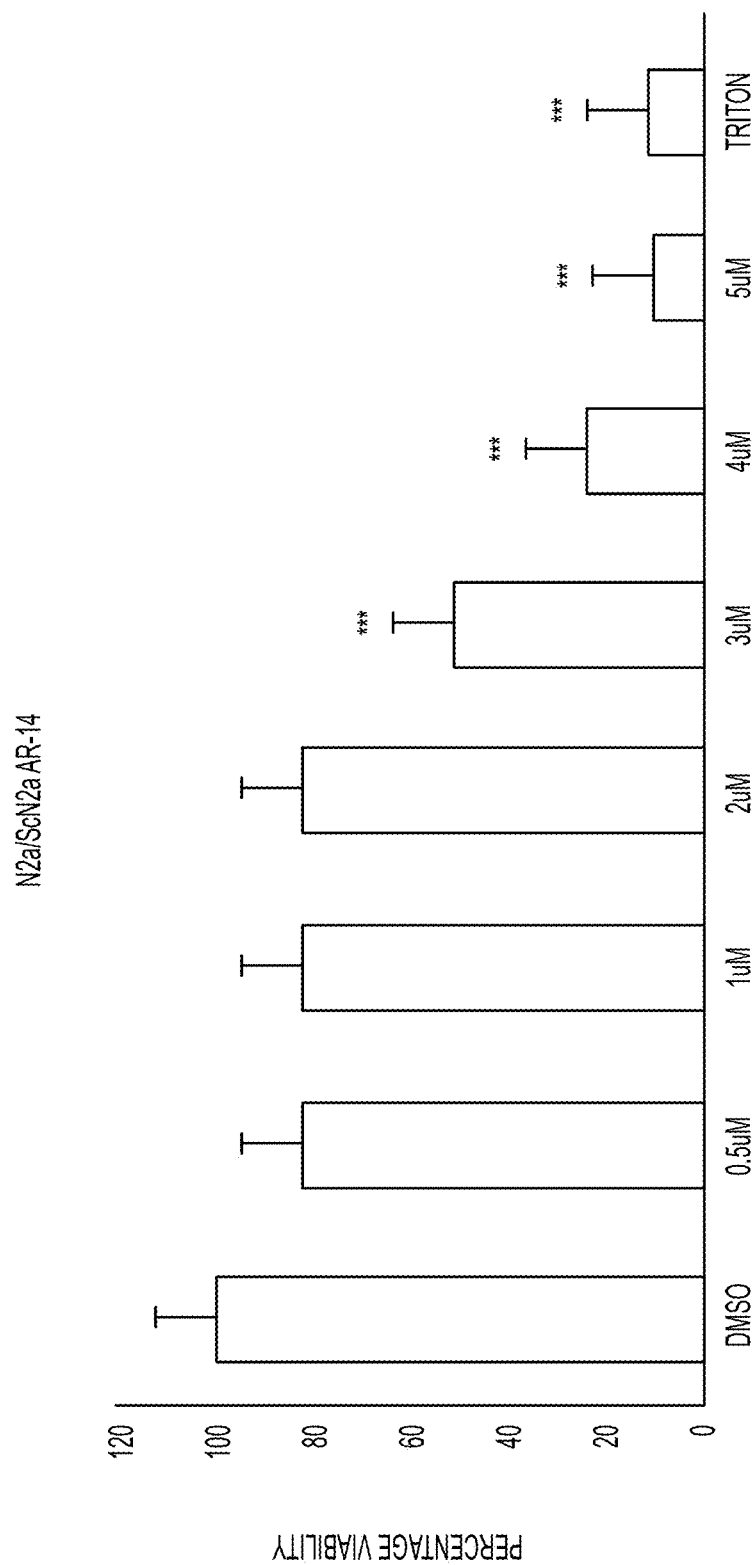
FIG. 5B illustrates an exemplary XTT Cytotoxicity Assay for control (DSMO) and six concentrations of AR-14; Triton X-100 treatment was used as a positive control (induction of cell death); asterisks indicate concentrations with statistically significant toxicity.

FIG. 5B shows that exposing AR-14 to the ScN2a cells was done at non-toxic concentrations (XTT toxicity assay).

Figure 5C:
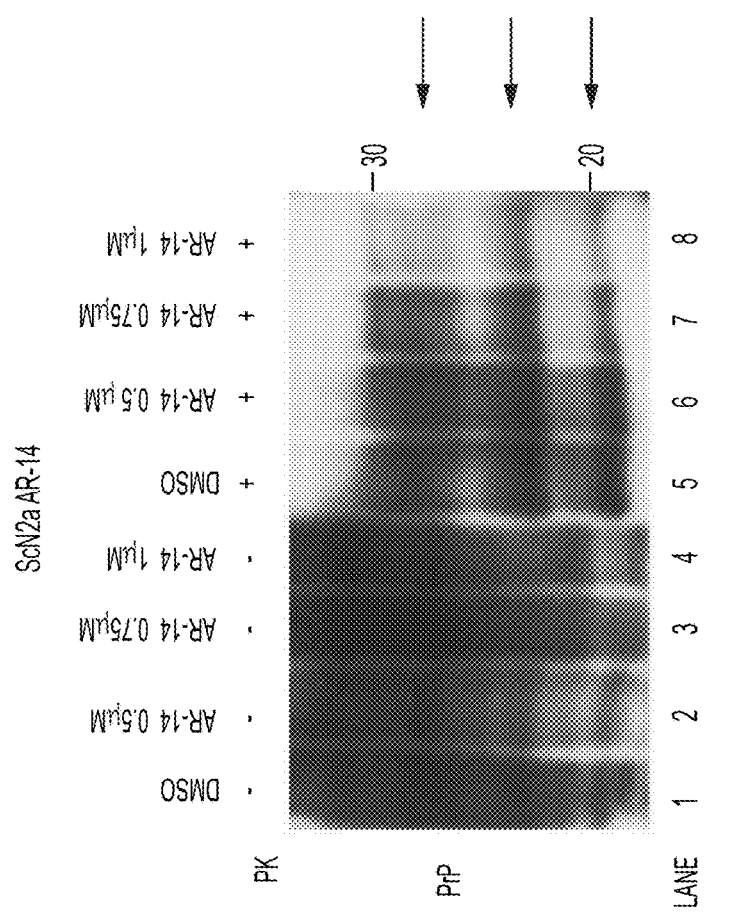
FIG. 5C is an exemplary immunoblot showing the PrP banding pattern for persistently prion infected ScN2A cells (prion strain 22L) treated for 72 hours with AR-14 at the indicated nanomolar concentrations, with or without PK.

FIG. 5C shows an exemplary effect of AR-14 on persistently prion infected ScN2a cells (prion strain 22L) at various nanomolar concentrations (0.5, 0.75 and 1.0 µM). PrP$^{Sc}$ (+PK, indicated by 3 arrows) was dose-dependently reduced, with AR-14 effective already at 0.75 µM. AR-14 showed anti-prion effects at nanomolar concentrations.

Figure 6A:
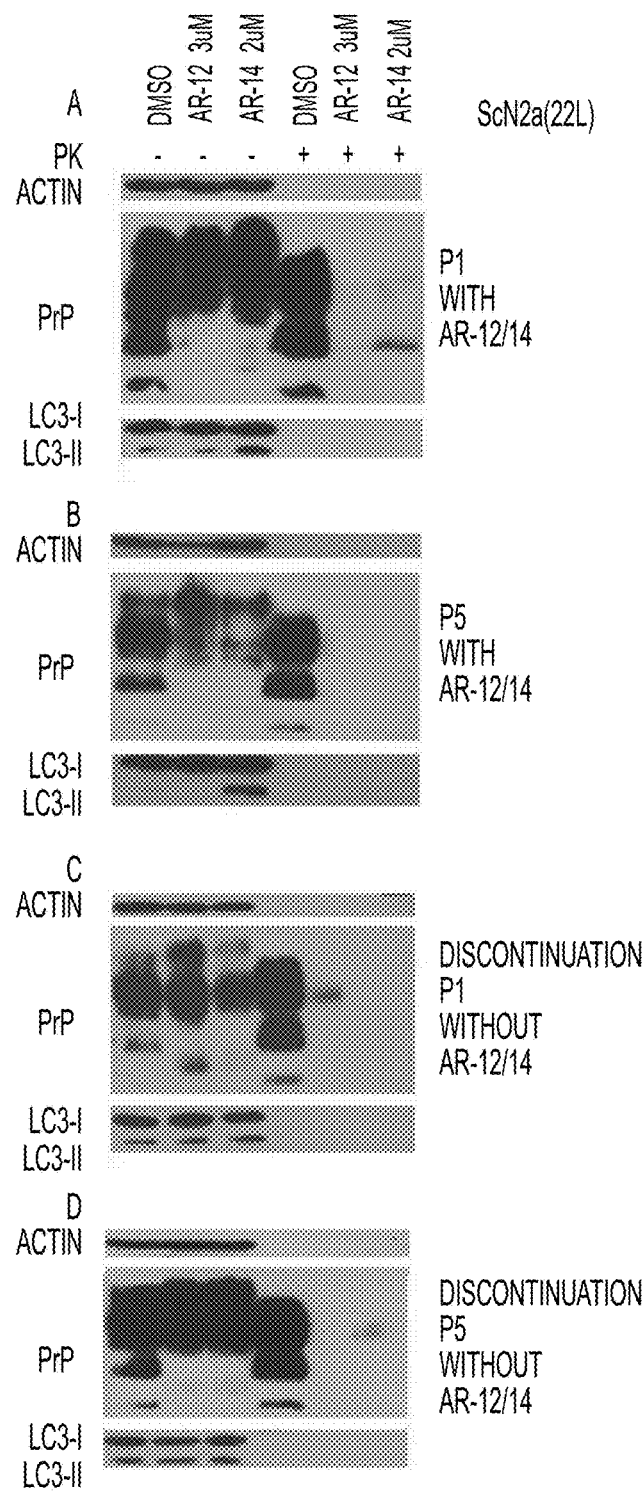
FIG. 6A is an exemplary immunoblot showing the PrP banding pattern (with or without PK) for persistently prion infected ScN2A cells treated with DMSO, AR-12 (3 µM) or AR-14 (2 µM) for 4 days (upper panel), 20 days (second panel), 20 days with drug, followed by 4 days without (third panel), and 20 days with drug, followed by 20 days without drug treatment (lower panel) with LC3-I/II used as marker for autophagy.

FIG. 6A shows that a long-term treatment of ScN2a cells with AR-12 and AR-14 cures the cells of prion infection. ScN2a cells (neuronal) were treated with AR-12 (3 µM) or AR-14 (2 µM). DMSO-treated cells were used as a control. Treatment was continued for 20 days (five passages). Then, the treatment was stopped, and cells were passaged for another 20 days (five passages) without drug. At passages one and five with treatment (first and second panel), or after drug-withdrawal (third and fourth panel), cells were lysed. Cell lysates were split into two halves, one half was treated with proteinase K (PK; 20 µg/ml, 30 min at 37° C.) and subjected to immunoblot analysis. The immunoblot was developed with anti-PrP mAb 4H11, anti-LC3 (autophagy marker) and anti-actin for gel loading. The PrP$^{Sc}$ signal completely disappeared during drug treatment and did not reappear after drug withdrawal.

Figure 6B:
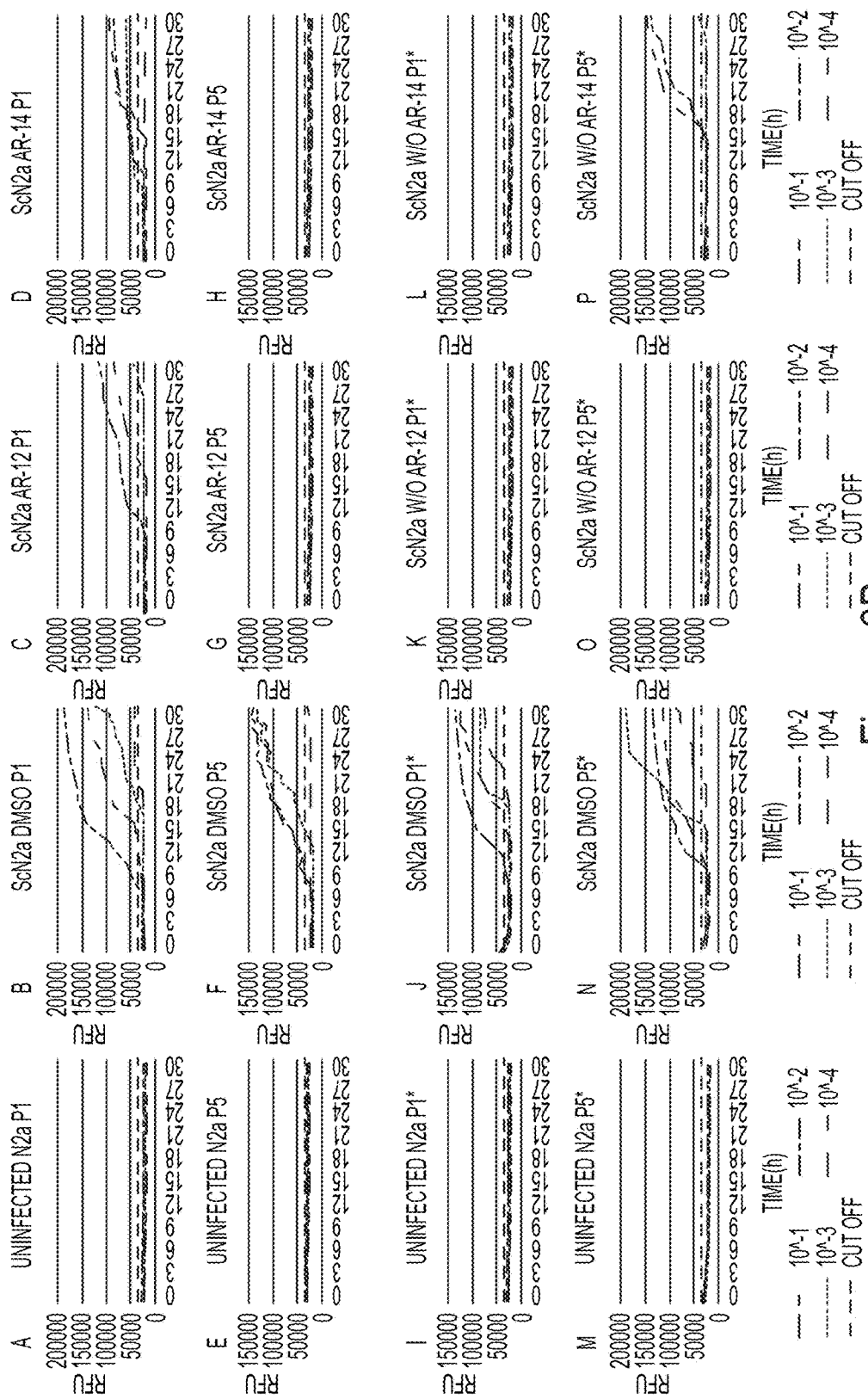
FIG. 6B is an exemplary RT-QuIC assay showing prion conversion activity in uninfected N2a cells (panels A, E, I and M), ScN2a cells treated with DMSO (panels B, F, J and N), ScN2a cells treated with 3 µM of AR-12 (panels C, G, K and O), and ScN2a cells treated with 2 µM of AR-14 (panels D, H, L and P) for 4 days (A-D), 20 days (E-H), 20 days with drug, followed by 4 days without (I-L), and 20 days with drug, followed by 20 days without drug treatment (M-P) with dilutions of cell lysates and the test cut-off indicated at the bottom.

FIG. 6B shows that prion conversion activity is lost in long-term AR-12 or AR-14 treated ScN2a cells. RT-QuIC assay was performed using recombinant mouse PrP as a substrate. Each quadruplicate RT-QuIC reaction was seeded with 2 µl cell lysate (at dilutions $10^{-1}$ to $10^{-4}$) of ScN2a cells treated with AR-12 (3 µM) (C, G), AR-14 (2 µM) (D, H) or solvent only (DMSO; B, F). Data shown are for passage one (P1) and passage five (P5). Uninfected N2a cells were used as negative test control (A, E). Panels in third and fourth row show ScN2a cells after treatment discontinuation for AR-12 (K, O), AR-14 (L, P) or solvent only (DMSO; J, N). Data shown are for passage one (P1) and passage five (P5) after drug withdrawal. Uninfected N2a cells were used as negative test control (I, M). The average increase of thioflavin-T fluorescence of replicate wells is plotted as a function of time. Y-axis represents relative fluorescent units (RFU) and x-axis time in hours. Cut-off values were shown as dotted line. ScN2a cells treated with AR-12 lost prion conversion activity (tested until passage five after terminating the AR-12 treatment).

Figure 6C:
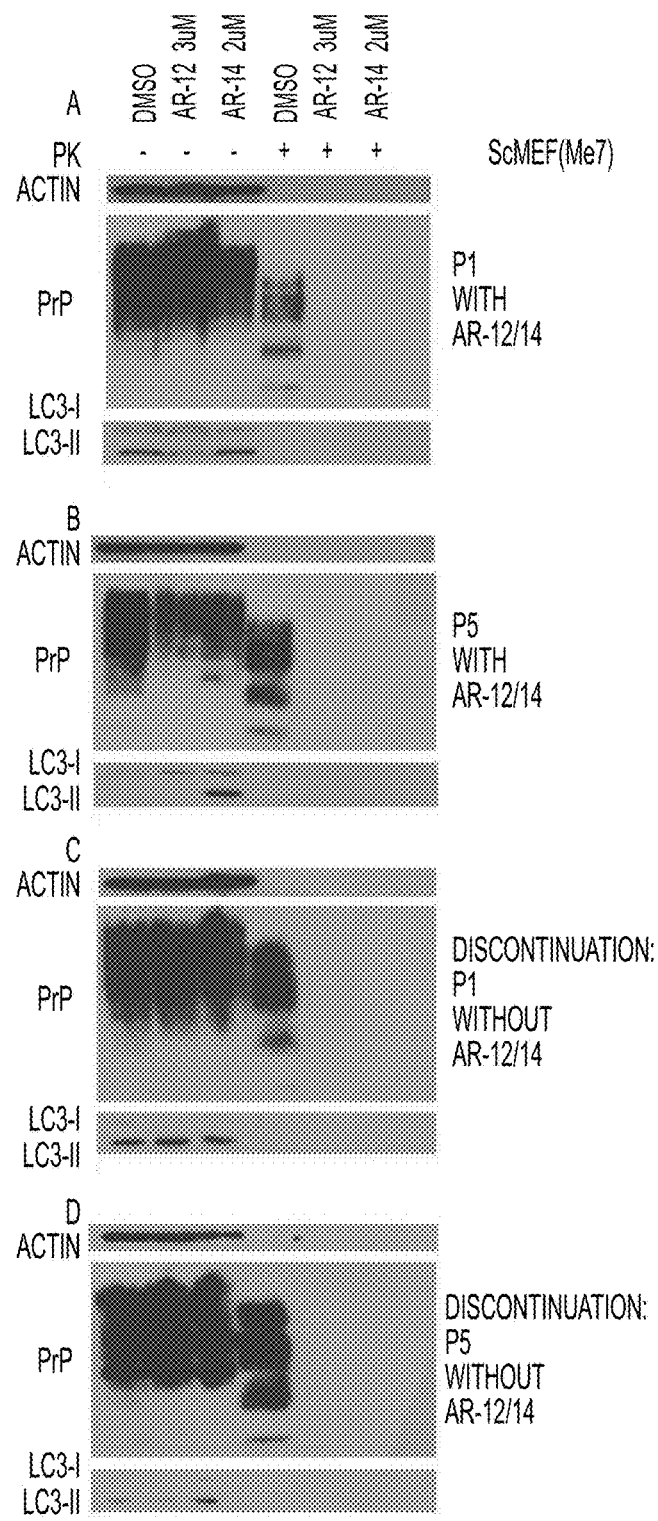
FIG. 6C is an exemplary immunoblot showing the PrP banding pattern (with or without PK) for persistently prion infected ScMEF cells (prion strain Me7) treated with DMSO, AR-12 (3 µM) or AR-14 (2 µM) for 4 days (upper panel), 20 days (second panel), 20 days with drug, followed by 4 days without (third panel), and 20 days with drug, followed by 20 days without drug treatment (lower panel) with LC3-I/II used as marker for autophagy.

FIG. 6C shows that a long-term treatment of ScMEF cells with AR-12 and AR-14 permanently cures the cells of prion infection. ScMEF cells (non-neuronal) were treated with AR-12 (3 µM) or AR-14 (2 µM). DMSO-treated cells were used as a control. Treatment was continued for 20 days (five passages). Then, the treatment was stopped, and cells were passaged for another 20 days (five passages) without drug. At passages one and five with treatment (first and second panel) or after drug-withdrawal (third and fourth panel), cells were lysed. Cell lysates were split into two halves, one half was treated with proteinase K (PK; 20 µg/ml, 30 min at 37° C.), and subjected to immunoblot analysis. The immunoblot was developed with anti-PrP mAb 4H11, anti-LC3

(autophagy marker) and anti-actin for gel loading. PrP$^{Sc}$ signal completely disappeared during drug treatment and did not reappear after drug withdrawal. Long-term treatment with AR-12 and AR-14 cured neuronal and non-neuronal cells from prion infection.

Figure 6D:
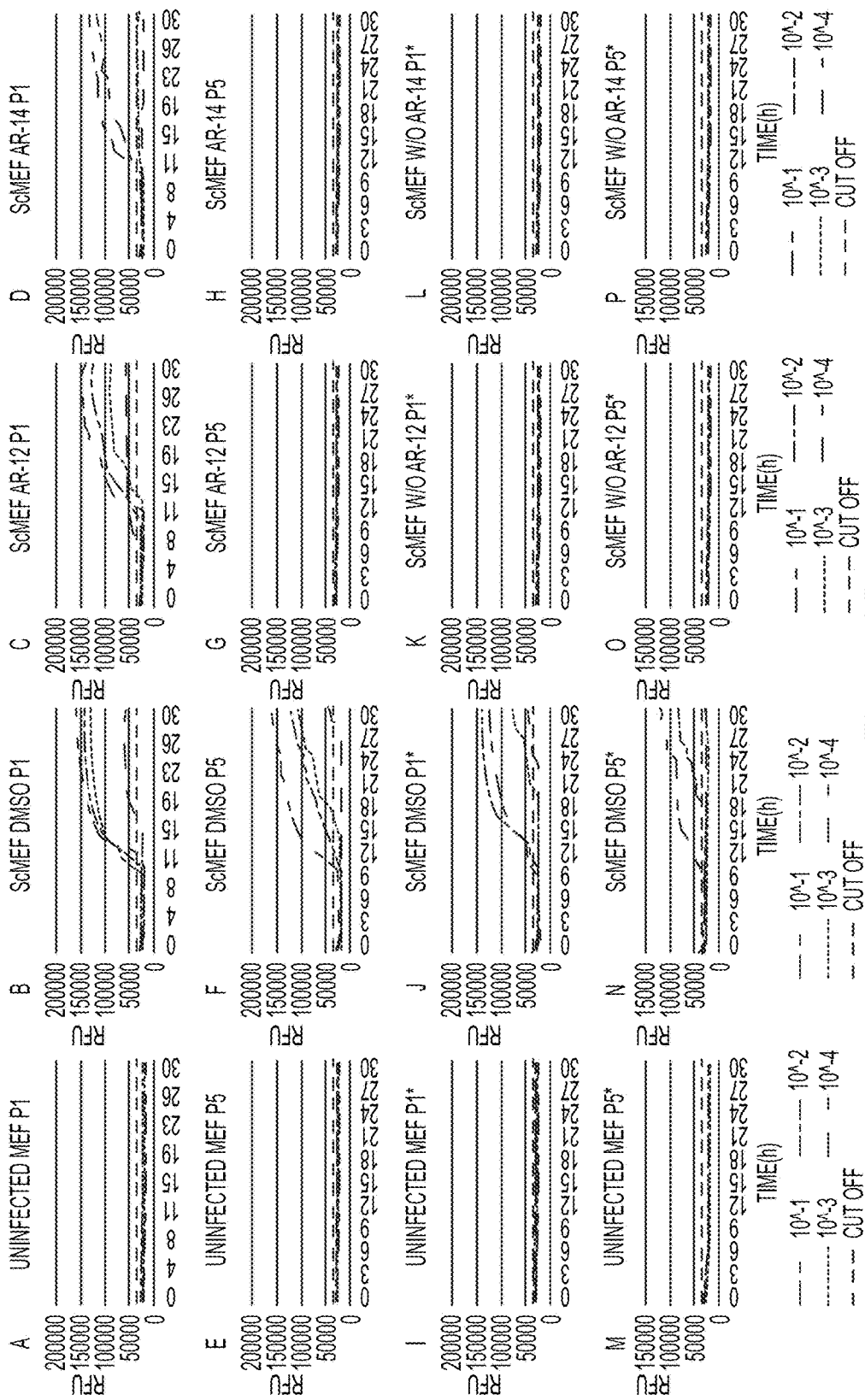
FIG. 6D is an exemplary RT-QuIC assay showing prion conversion activity in uninfected MEF cells (panels A, E, I and M), ScMEF cells treated with DMSO (panels B, F, J and N), ScMEF cells treated with 3 µM of AR-12 (panels C, G, K and O), and ScMEF cells treated with 2 µM of AR-14 (panels D, H, L and P) for 4 days (A-D), 20 days (E-H), 20 days with drug, followed by 4 days without (I-L), and 20 days with drug, followed by 20 days without drug treatment (M-P) with dilutions of cell lysates and the test cut-off indicated at the bottom.

FIG. 6D shows that prion conversion activity is lost in long-term AR-12 or AR-14 treated ScMEF cells. RT-QuIC assay was performed using recombinant mouse PrP as substrate. Each quadruplicate RT-QuIC reaction was seeded with 2 µl cell lysate (at dilutions $10^{-1}$ to $10^{-4}$) of ScMEF cells treated with AR-12 (3 µM) (C, G), AR-14 (2 µM) (D, H) or solvent only (DMSO; B, F). Data shown are for passage one (P1) and passage five (P5). Uninfected MEF cells were used as negative assay control (A, E). Panels in third and fourth row show ScMEF cells after treatment discontinuation for AR-12 (K, O), AR-14 (L, P) or solvent only (DMSO; J, N). Data shown are for passage one (P1) and passage five (P5) after drug withdrawal. Uninfected MWF cells were used as negative test control (I, M). The average increase of thioflavin-T fluorescence of replicate wells is plotted as a function of time. Y-axis represents relative fluorescent units (RFU) and x-axis time in hours. Cut-off values are shown as dotted lines. ScMEF cells treated with AR-12 or AR-14 lost prion conversion activity (tested until passage five after terminating the AR-12 treatment).

Figure 7:
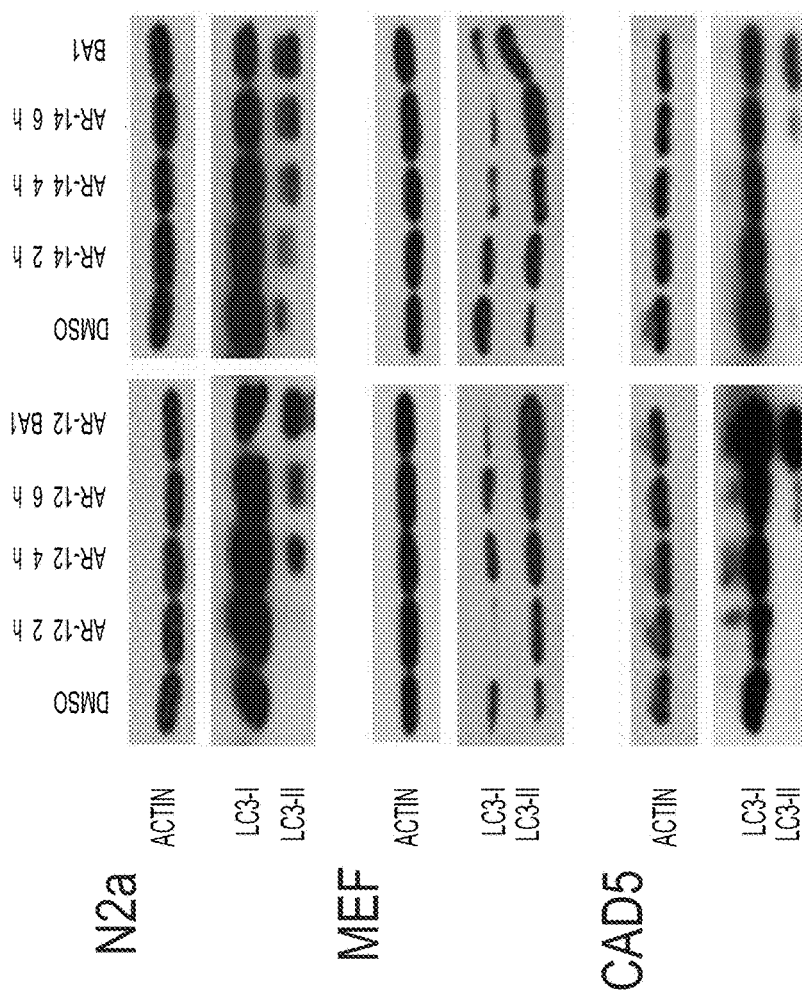
FIG. 7 is an exemplary immunoblot showing induction of autophagy by short-term treatment (2, 4 and 6 hours) with AR-12 (3 µM) or AR-14 (2 µM) in N2a, MEF and CAD5 cells; DMSO treatment was used as negative control; actin (upper panel) served as a loading control; Increase of LC3-II band indicates autophagy induction and treatment with bafilomycin A1 (BA1) used to block autophagy flux.

FIG. 7 shows that AR-12 and AR-14 induce autophagy in N2a, MEF and CAD5 cells, indicating that AR-12 and AR-14-mediated anti-prion effect involve autophagy. N2a, MEF and CAD5 cells were treated with either AR-12 (3 µM) or AR-14 (2 respectively, for 2, 4 or 6 hours. Bafilomycin A1 treatment was used to alter the lysosomal function and to block the autophagic flux. This control demonstrates that AR-12 and AR-14 induce autophagy and do not block autophagic flux. Solvent only-treated cells (DMSO) were used as treatment vehicle control. Cells were lysed, subjected to immunoblot analysis, and the immunoblots were developed with an anti-LC3 mAb as autophagy marker and an actin mAb (gel loading control; upper panel). Both AR-12 and AR-14 showed a time dependent and pronounced increase in LC3-II levels (lower band). This induction was lower than that of BA1-treated cells, which had the highest expression level of LC3-II due to blocking of autophagic flux and lysosomal function. These data indicate that AR-12 and AR-14 are strong inducers of autophagy in all three tested cell lines. Interestingly, the lowest induction was found in CAD5 cells, which correlates with the weakest effects on PrP$^{Sc}$ levels in these cells. Formal testing of the impact of autophagy was done using cells compromised in autophagy and comparing them to wild-type cells (see FIGS. 8A and 8C).

FIG. 8A shows the establishment of N2a cells with a knock-out in the autophagy gene ATG5. Using CRISPR/Cas-9 technology, insertions and deletions were introduced into exon 5 and 6 of the ATG5 gene, resulting in premature stop codons. Individual cell clones were generated and analyzed for ATG5 knock-out by DNA sequencing and immunoblot analysis. Various positive clones were then persistently infected with prions (strain 22L). Immunoblot shows ATG5-KO ScN2a cells, probed for Atg5, LC3 and actin. There is no Atg5 and LC3-II band (lane 1 vs. lane 2), indicating knock-out of ATG5 and complete deficiency in autophagy.

Figure 8B:
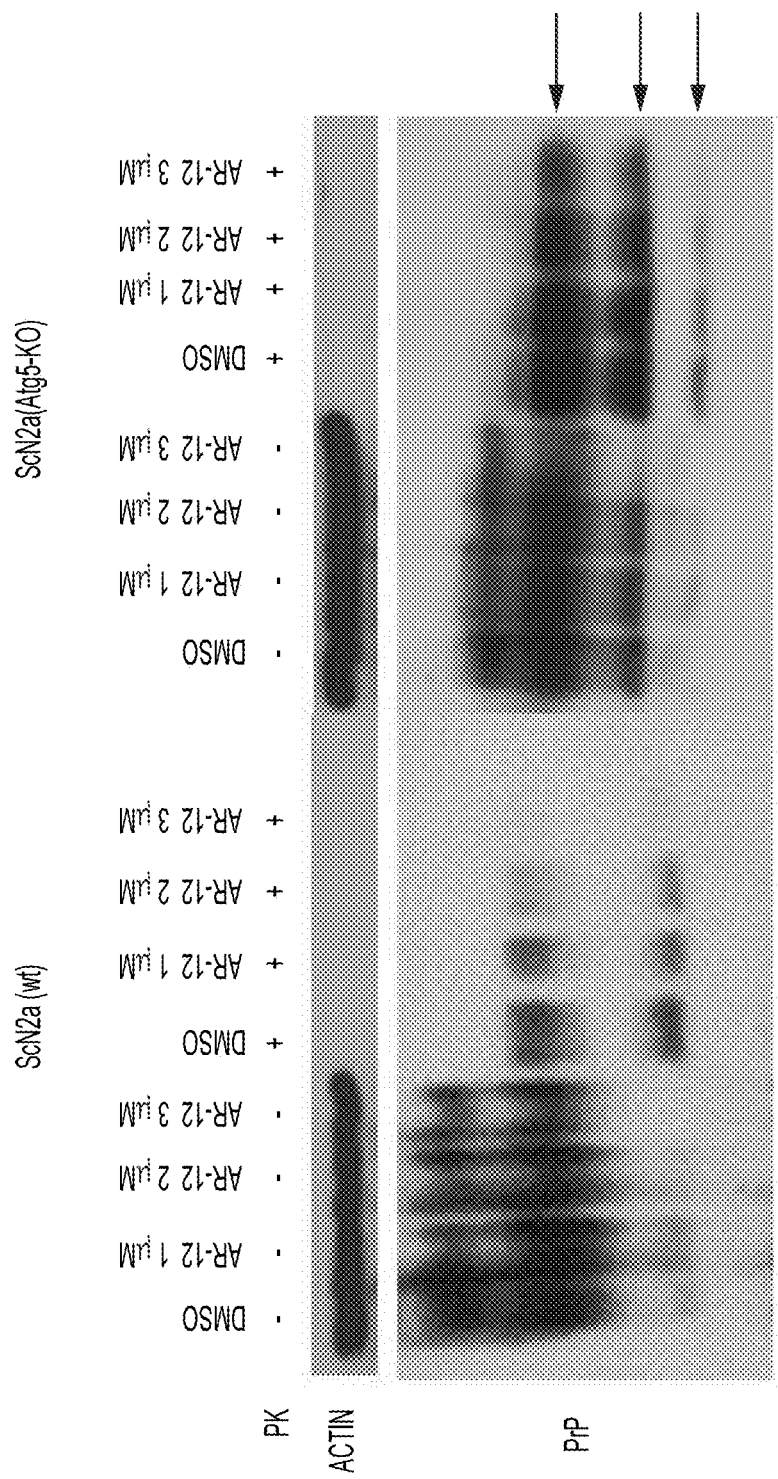
FIG. 8B is an exemplary immunoblot showing the PrP banding pattern for wild-type ScN2A cells (left panel) and autophagy-deficient Atg5-KO ScN2a cells (right panel) after treatment with control (DSMO) or AR-12 at three concentrations, with or without PK and actin used as a loading control.

FIG. 8B shows the kinetics of AR-12 mediated reduction of PrP$^{Sc}$ in wild-type and Atg5-KO ScN2a cells, indicating partial involvement of autophagy competency in AR-12 mediated anti-prion effects. Persistently prion infected wild-type (left panel) and ATG5-KO (right panel) ScN2a cells were treated for 72 hours with 1 to 3 µM AR-12 and the cells subjected to immunoblot analysis. Solvent only-treated cells (DMSO) were used as control. Cell lysates were split into two halves, and one half was treated with proteinase K (PK; 20 µl/ml, 30 min at 37° C.) and subjected to SDS-PAGE and immunoblot analysis. The immunoblot was developed with anti-PrP mAb 4H11, and the blot was re-probed with mAb for actin (gel loading; upper panel). PrP$^{Sc}$ (right side of panels, +PK; indicated by 3 arrows) was reduced in both situations, although with different kinetics for wild-type and Atg5-KO ScN2a cells. At 3 µM of AR-12, the reduction of PrP$^{Sc}$ in wild-type ScN2a cells was 90% or greater, while in Atg5-KO ScN2a cells, the reduction was about 50%. These results indicate autophagy competency is involved in AR-12 mediated anti-prion effects.

FIG. 8C shows the kinetics of AR-14 mediated reduction of PrP$^{Sc}$ in wild-type and Atg5-KO ScN2a cells, indicating partial involvement of autophagy competency in AR-14 mediated anti-prion effects. Persistently prion infected wild-type (left panel) and ATG5-KO (right panel) ScN2a cells were treated for 72 hours with 0.5, 1 and 2 µM AR-14 and the cells subjected to immunoblot analysis. Solvent only-treated cells (DMSO) were used as control. Cell lysates were split into two halves, and one half was treated with proteinase K (PK; 20 µl/ml, 30 min at 37° C.) and subjected to SDS-PAGE and immunoblot analysis. The immunoblot was developed with anti-PrP mAb 4H11, and the blot was re-probed with mAb for actin (gel loading; upper panel). PrP$^{Sc}$ (right side of panels, +PK; indicated by 3 arrows) was reduced in both situations, although with different kinetics for wild-type and Atg5-KO ScN2a cells. At 2 µM AR-14, the reduction of PrP$^{Sc}$ in wild-type ScN2a cells was 100%, whereas in Atg5-KO ScN2a cells, the reduction was about 50%. These results indicate autophagy competency is involved in AR-14 mediated anti-prion effects.

AR-12 or AR-14, as described herein, can be administered orally, parenterally (IV, IM, depot-IM, SQ, and depot-SQ), sublingually, intranasally (inhalation), intrathecally, topically, in the pulmonary system or airways (e.g., nebulization, aerosol) or rectally. Dosage forms known to those of skill in the art are suitable for delivery of AR-12 and AR-14 described herein. In one aspect, AR-12 and AR-14 is administered orally.

AR-12 or AR-14 can be formulated into suitable pharmaceutical preparations such as creams, gels, suspensions, tablets, capsules, or elixirs for oral administration or in sterile solutions or suspensions for parenteral administration. AR-12 or AR-14 can be formulated into pharmaceutical compositions using techniques and procedures well-known in the art.

In one aspect, about 0.1 to 1000 mg, about 5 to about 100 mg, or about 10 to about 50 mg of the AR-12 or AR-14, or a physiologically acceptable salt or ester can be compounded with a physiologically acceptable vehicle, carrier, excipient, binder, preservative, pain reliever, stabilizer, flavor, etc., in a unit dosage form as called for by accepted pharmaceutical practice. The amount of active substance in compositions or preparations comprising AR-12 or AR-14 is such that a suitable dosage and concentration in a host in the range indicated is obtained.

In another aspect, the compositions can be formulated in a unit dosage form, each dosage containing from about 1 to about 1000 mg, about 1 to about 500 mg, or about 10 to about 100 mg of the active ingredient. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient.

In one aspect, AR-12 or AR-14 alone or AR-12 or AR-14 and one or more additional active or inert ingredients, is mixed with a suitable pharmaceutically acceptable carrier to form a composition. Upon mixing or addition of the compound(s), the resulting mixture may be a cream, gel, solution, suspension, emulsion, or the like. Liposomal suspensions may also be used as pharmaceutically acceptable carriers. These may be prepared according to methods known to those skilled in the art. The form of the resulting mixture depends upon a number of factors, including the intended mode of administration and the solubility of the compound in the selected carrier or vehicle. In one aspect, the effective concentration is sufficient for lessening or ameliorating at least one symptom of the disease, disorder, or condition treated and may be empirically determined.

Pharmaceutical carriers or vehicles suitable for administration of AR-12 or AR-14 described herein include any such carriers suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients (e.g., Congo Red, anthracyclines, sulfated polyanions, suramin, imatinib/ Gleevec®, rapamycin, trehalose, lithium, tamoxifen, piperazine derivatives, diphenylpyrazole-derived compounds, flupirtine, tetrapyrroles, quinacrine, chlorpromazine, pentosan polysulphate, D-penicillamine, active and passive anti-prion vaccination, doxycycline, donepezil, rivastigmine, galantamine and memantine).

In another aspect, if AR-12 or AR-14 exhibits insufficient solubility, methods for solubilizing may be used. Such methods are known and include, but are not limited to, using co-solvents such as dimethylsulfoxide (DMSO), using surfactants such as TWEEN, and dissolution in aqueous sodium bicarbonate. Derivatives of the compounds, such as salts or prodrugs, may also be used in formulating effective pharmaceutical compositions.

The concentration of the compound is effective for delivery of an amount upon administration that lessens or ameliorates at least one symptom of the disorder for which the compound is administered. Typically, the compositions are formulated for single dosage administration.

In another aspect, AR-12 or AR-14 as described herein may be prepared with carriers that protect them against rapid elimination from the body, such as time-release formulations or coatings. Such carriers include controlled release formulations, such as, but not limited to, microencapsulated delivery systems. The active compound can be included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder.

In another aspect, AR-12 or AR-14 and compositions described herein can be enclosed in multiple or single dose containers. The enclosed compounds and compositions can be provided in kits, for example, including component parts that can be assembled for use. For example, AR-12 or AR-14 in lyophilized form and a suitable diluent may be provided as separated components for combination prior to use. A kit may include AR-12 and a second therapeutic agent for co-administration. AR-12 and second therapeutic agent may be provided as separate component parts. A kit may include a plurality of containers, each container holding one or more unit dose of AR-12 or AR-14 described herein. In one aspect, the containers can be adapted for the desired mode of administration, including, but not limited to suspensions, tablets, gel capsules, sustained-release capsules, and the like for oral administration; depot products, pre-filled syringes, ampoules, vials, and the like for parenteral administration; and patches, medipads, gels, suspensions, creams, and the like for topical administration.

The concentration of AR-12 or AR-14 in the pharmaceutical composition will depend on absorption, inactivation, and excretion rates of the active compound, the dosage schedule, and amount administered as well as other factors known to those of skill in the art.

In another aspect, the active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound can be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

The active materials can also be mixed with other active materials that do not impair the desired action, or with materials that supplement the desired action. AR-12 or AR-14 can be used, for example, in combination with an antibiotic, antifungal, antiviral, pain reliever, or cosmetic.

In one aspect, solutions or suspensions used for parenteral, intradermal, subcutaneous, inhalation, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, alcohols, polyethylene glycol, glycerin, propylene glycol, or other synthetic solvent; antimicrobial agents such as benzyl alcohol and methyl parabens; antioxidants such as ascorbic acid and sodium bisulfate; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, intramuscularly, or intraperitoneally, suitable carriers include, but are not limited to, physiological saline, phosphate buffered saline (PBS), and solutions containing thickening and solubilizing agents such as glucose, polyethylene glycol, polypropylene glycol, ethanol, N-methylpyrrolidone, surfactants and mixtures thereof. Liposomal suspensions including tissue-targeted liposomes may also be suitable as pharmaceutically acceptable carriers. These may be prepared according to methods known in the art.

In another aspect, AR-12 or AR-14 may be prepared with carriers that protect the compound against rapid elimination from the body, such as time-release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

In yet another aspect, compounds employed in the methods of the disclosure may be administered enterally or parenterally. When administered orally, compounds employed in the methods of the disclosure can be administered in usual dosage forms for oral administration as is well known to those skilled in the art. These dosage forms include the usual solid unit dosage forms of tablets and capsules as well as liquid dosage forms such as solutions, suspensions, and elixirs. When the solid dosage forms are used, they can be of the sustained release type so that the compounds employed in the methods described herein need to be administered only once or twice daily.

The dosage forms can be administered to the patient (e.g., human or non-human animal) 1, 2, 3, or 4 times daily. AR-12 or AR-14 as described herein can be administered either three or fewer times, or even once or twice daily or every other day.

The terms "therapeutically effective amount" and "therapeutically effective period of time" are used to denote treatments at dosages and for periods of time effective to reduce the prion infection in cells, tissues or organs. As noted above, such administration can be parenteral, oral, sublingual, transdermal, topical, intranasal, or intrarectal. In one aspect, when administered systemically, the therapeutic composition can be administered at a sufficient dosage to attain a blood level of the compounds of from about 0.1 µM to about 20 µM. For localized administration, much lower concentrations than this can be effective, and much higher concentrations may be tolerated. One of skill in the art will appreciate that such therapeutic effect resulting in a lower effective concentration of AR-12 or AR-14 may vary considerably depending on the tissue, organ, or the particular animal or patient to be treated. It is also understood that while a patient may be started at one dose, that dose may be varied overtime as the patient's condition changes.

It should be apparent to one skilled in the art that the exact dosage and frequency of administration will depend on the particular compounds employed in the methods of the disclosure administered, the particular condition being treated, the severity of the condition being treated, the age, weight, general physical condition of the particular patient, and other medication the individual may be taking as is well known to administering physicians or veterinarians who are skilled in this art.

Not every element described herein is required. Indeed, a person of skill in the art will find numerous additional uses of and variations to the methods described herein, which the inventors intend to be limited only by the claims. All references cited herein are incorporated by reference in their entirety.

REFERENCES

1. Prusiner, S. B. (1982). *Science* 216, 136-144.
2. Prusiner, S, B, (1998). *Proc. Natl. Acad. Sci. USA* 95, 13363-13383.
3. Nunziante, M., Gilch, S., Schatzl, H. M. (2003). *Chembiochem*. 4, 1268-1284.
4. Gilch, S., Krammer, C., Schatzl, H. M. (2008). *Expert Opin. Biol. Ther.* 8, 923-940.
5. Krammer, C., Vorberg, I, Schatzl, H. M., Gilch, S. (2009). *Infect. Disord. Drug Targets* 9, 3-14.
6. Ertmer, A., Gilch, S., Yun, S. W., Flechsig, E., Klebl, B., Stein-Gerlach, M., Klein, M. A., Schatzl, H. M. (2004). *J. Biol. Chem.* 279, 41918-41927.
7. Ertmer, A., Huber, V., Gilch, S., Yoshimori, T., Erfle, V., Duyster, J., Elsasser, H. P., Schatzl, H. M. (2007). *Leukemia* 21, 936-942.
8. Aguib, Y., Heiseke, A., Gilch, S., Riemer, C., Baier, M., Schatzl, H. M., Ertmer, A. (2009). *Autophagy* 5, 361-369.
9. Heiseke, A., Aguib, Y., Riemer, C., Baier, M., Schatzl, H. M. (2009). *J. Neurochem.* 109, 25-34.
10. Heiseke, A., Aguib, Y., Schatzl, H. M. (2010). *Curr. Issues Mol. Biol.* 12, 87-98.
11. Schatzl, H., Laszlo, L., Holtzman, D. M., Tatzelt, J. Weiner, R. I., Mobley, W., Prusiner, S. B. (1997). *J. Virol.* 71, 8821-8831.
12. Gilch, S., K. F. Winklhofer, M. H. Groschup, M. Nunziante, R. Lucassen, C. Spielhaupter, W. Muranyi, D. Riesner, J. Tatzelt, H. M. Schatzl. (2001). *EMBO J.* 20, 3957-3366.
13. Taguchi, Y., Mistica, A. M., Kitamoto, T., Schatzl, H. M. (2013) *PLoS Pathog.* 9, e1003466.
14. Maas, E., Geissen, M., Groschup, M. H., Rost, R., Onodera, T., Schatzl, H. M., Vorberg I. (2007). *J. Biol. Chem.* 282, 18702-18710.
15. Qi, Y., Wang, J. K., McMillian, M., Chikaraishi, D. M. (1997). *J. Neurosci.* 17, 1217-1225.

16. Kuma, A., Hatano, M., Matsui, M., Yamamoto, A., Nakaya, H., Yoshimori, T., Ohsumi, Y., Tokuhisa, T., Mizushima, N. (2004). *Nature* 432, 1032-1036.
17. Orru, C. D., Wilham, J. M., Vascellari, S., Hughson, A. G., Caughey, B. (2012). *Prion* 6, 147-152.
18. John, T. R., Schatzl, H. M., Gilch, S. (2013). *Prion* 7, 253-258.

What is claimed as new and desired to be protected by Letters Patent of the United States is:

1. A method of reducing the level of prions in prion-infected cells, tissues or organs, comprising exposing prion-infected cells, tissues or organs to AR-12 in an amount sufficient to reduce the level of prions in the prion-infected cells, tissues or organs by at least about 50% compared to prion-infected cells, tissues, organs that have not been exposed to AR-12.

2. The method of claim 1, wherein the prion level is reduced by at least about 90%.

3. The method of claim 2, wherein prion infected cells, tissues or organs are exposed to a concentration of AR-12 of at least about 1 µM.

4. The method of claim 3, wherein prion infected cells, tissues or organs are exposed to a concentration of AR-12 between about 1 µM and 3 µM.

5. The method of claim 1, wherein the amount of AR-12 the prion infected cells, tissues, and organs are exposed to is sufficient to reduce the prion level by at least about 50% to about 100%.

6. The method of claim 5, wherein the amount of AR-12 is non-toxic.

7. A method of reducing the level of prions in prion-infected cells, tissues or organs, comprising exposing prion-infected cells, tissues or organs to AR-14 in amount sufficient to reduce the level of prions in the prion-infected cells, tissues or organs by at least about 50% compared to prion-infected cells, tissues, organs that have not been exposed to AR-14.

8. The method of claim 7, wherein prion infected cell, or organs are exposed to a concentration of AR-14 of at least about 1 µM.

9. The method of claim 8, wherein prion infected cells, tissues or organs are exposed to a concentration of AR-14 between about 0.5 µM and 2 µM.

10. The method of claim 8, wherein prion infected cells, tissues or organs are exposed to AR-14 in an amount sufficient to achieve a concentration of AR-14 between about 0.5 µM and 2 µM in the prion infected cells, tissues, or organs.

11. The method of claim 7, wherein the amount of AR-14 the prion infected cells, tissues, and organs are exposed to is sufficient to reduce the prion level by at least about 50% to about 100%.

12. The method of claim 11, wherein the amount of AR-14 is non-toxic.

\* \* \* \* \*

UNITED STATES PATENT AND TRADEMARK OFFICE
CERTIFICATE OF CORRECTION

PATENT NO. : 9,974,771 B2
APPLICATION NO. : 15/445964
DATED : May 22, 2018
INVENTOR(S) : Hermann M. Schaetzl et al.

Page 1 of 1

It is certified that error appears in the above-identified patent and that said Letters Patent is hereby corrected as shown below:

In the Specification

Column 1, Line 14 add Government Support Clause:
-- This invention was made with government support under grant number CA094829 awarded by the National Institutes of Health and grant number DAMD17-02-1-0117 awarded by the United States Army Medical Research and Materiel Command. The government has certain rights in the invention. --

Signed and Sealed this
Tenth Day of November, 2020

Andrei Iancu
*Director of the United States Patent and Trademark Office*